(12) United States Patent
Adams

(10) Patent No.: US 8,524,501 B2
(45) Date of Patent: *Sep. 3, 2013

(54) SELF-SENSING ARRAY OF MICROCANTILEVERS FOR CHEMICAL DETECTION

(75) Inventor: Jesse D. Adams, Reno, NV (US)

(73) Assignee: Board of Regents of the Nevada System of Higher Education, Reno, NV (US)

(*) Notice: Subject to any disclaimer, the term of this patent is extended or adjusted under 35 U.S.C. 154(b) by 0 days.

This patent is subject to a terminal disclaimer.

(21) Appl. No.: 13/350,921

(22) Filed: Jan. 16, 2012

(65) Prior Publication Data

US 2012/0115757 A1 May 10, 2012

Related U.S. Application Data

(63) Continuation of application No. 11/845,680, filed on Aug. 27, 2007, now abandoned, and a continuation of application No. 10/967,748, filed on Oct. 15, 2004, now abandoned.

(60) Provisional application No. 60/512,504, filed on Oct. 17, 2003.

(51) Int. Cl.
*C40B 60/12* (2006.01)

(52) U.S. Cl.
USPC ............ 436/22; 422/88; 73/24.06; 438/694; 506/39

(58) Field of Classification Search
USPC ............ 422/88; 506/39; 73/24.1; 438/694; 436/22
See application file for complete search history.

(56) References Cited

U.S. PATENT DOCUMENTS

| 3,164,004 A | 1/1965 | King |
| 3,266,291 A | 8/1966 | King |
| 3,478,573 A * | 11/1969 | King, Jr. ................ 73/24.04 |

(Continued)

FOREIGN PATENT DOCUMENTS

| GB | 2432001 | 4/2009 |
| GB | 2437753 | 4/2009 |

(Continued)

OTHER PUBLICATIONS

Kim., B.H. Parallel Frequency Readout of an Array of MAss-Sensitive Transducers for Sensor Applications.(2000). pp. 229-232.*

(Continued)

*Primary Examiner* — Krishnan S Menon
*Assistant Examiner* — Rebecca M Fritchman
(74) *Attorney, Agent, or Firm* — Wood, Herron & Evans, LLP

(57) ABSTRACT

The invention provides a chemical detection system for detecting at least one target chemical species, including a self-sensed cantilevered probe array having a plurality of self-sensed cantilevered probes, at least one chemical-sensitive coating material applied to at least one cantilevered probe in the cantilevered probe array, and an interface circuit that is coupled to the cantilevered probe array. At least one cantilevered probe in the cantilevered probe array exhibits a shifted cantilevered probe response when the cantilevered probe array is exposed to the target chemical species and the interface circuit actuates the cantilevered probe. A handheld chemical detection system and a method of operation are also disclosed.

20 Claims, 11 Drawing Sheets

(56) References Cited

U.S. PATENT DOCUMENTS

| | | |
|---|---|---|
| 3,715,911 A | 2/1973 | Chuan |
| 4,312,288 A | 1/1982 | Finsterwalder et al. |
| 4,549,427 A | 10/1985 | Kolesar, Jr. |
| 4,637,987 A | 1/1987 | Minten et al. |
| 4,674,319 A | 6/1987 | Muller et al. |
| 4,747,698 A | 5/1988 | Wickramasinghe et al. |
| 4,935,634 A | 6/1990 | Hansma et al. |
| 4,992,244 A | 2/1991 | Grate |
| 5,187,367 A | 2/1993 | Miyazaki et al. |
| 5,266,801 A | 11/1993 | Elings et al. |
| 5,345,213 A | 9/1994 | Semancik et al. |
| 5,356,756 A | 10/1994 | Cavicchi et al. |
| 5,411,709 A | 5/1995 | Furuki et al. |
| 5,412,980 A | 5/1995 | Elings et al. |
| 5,445,008 A | 8/1995 | Wachter et al. |
| 5,469,369 A | 11/1995 | Rose-Pehrsson et al. |
| 5,519,212 A | 5/1996 | Elings et al. |
| 5,719,324 A * | 2/1998 | Thundat et al. .............. 73/24.01 |
| 5,742,377 A | 4/1998 | Minne et al. |
| 5,750,989 A | 5/1998 | Lindsay et al. |
| 5,753,814 A | 5/1998 | Han et al. |
| 5,756,631 A | 5/1998 | Grate |
| 5,807,758 A | 9/1998 | Lee et al. |
| 5,874,668 A | 2/1999 | Xu et al. |
| 5,883,705 A | 3/1999 | Minne et al. |
| 5,918,263 A | 6/1999 | Thundat |
| 5,965,452 A | 10/1999 | Kovacs |
| 6,005,400 A | 12/1999 | Thundat et al. |
| 6,015,869 A | 1/2000 | Grate et al. |
| 6,016,686 A | 1/2000 | Thundat |
| 6,029,500 A | 2/2000 | Tom |
| 6,032,518 A | 3/2000 | Prater et al. |
| 6,041,642 A | 3/2000 | Duncan |
| 6,050,722 A | 4/2000 | Thundat et al. |
| 6,075,585 A | 6/2000 | Minne et al. |
| 6,096,559 A | 8/2000 | Thundat et al. |
| 6,118,124 A | 9/2000 | Thundat et al. |
| 6,156,578 A | 12/2000 | Tom |
| 6,167,748 B1 | 1/2001 | Britton, Jr. et al. |
| 6,182,499 B1 | 2/2001 | McFarland et al. |
| 6,185,992 B1 | 2/2001 | Daniels et al. |
| 6,189,374 B1 | 2/2001 | Adderton et al. |
| 6,212,939 B1 | 4/2001 | Thundat |
| 6,253,162 B1 | 6/2001 | Jarman et al. |
| 6,263,736 B1 | 7/2001 | Thundat et al. |
| 6,269,685 B1 | 8/2001 | Oden |
| 6,280,939 B1 | 8/2001 | Allen |
| 6,289,717 B1 | 9/2001 | Thundat et al. |
| 6,295,861 B1 | 10/2001 | Tom et al. |
| 6,311,549 B1 | 11/2001 | Thundat et al. |
| 6,311,557 B1 | 11/2001 | Davis et al. |
| 6,312,959 B1 | 11/2001 | Datskos |
| 6,336,353 B2 | 1/2002 | Matsiev et al. |
| 6,336,366 B1 | 1/2002 | Thundat et al. |
| 6,393,895 B1 | 5/2002 | Matsiev et al. |
| 6,401,519 B1 | 6/2002 | McFarland et al. |
| 6,408,250 B1 | 6/2002 | Grate et al. |
| 6,411,075 B1 | 6/2002 | Battiston et al. |
| 6,436,346 B1 | 8/2002 | Doktycz et al. |
| 6,437,328 B1 | 8/2002 | Knauss et al. |
| 6,455,319 B1 | 9/2002 | Lewis et al. |
| 6,457,360 B1 | 10/2002 | Daraktchiev et al. |
| 6,469,293 B1 | 10/2002 | Shimizu et al. |
| 6,477,479 B1 | 11/2002 | Mansky et al. |
| 6,487,523 B2 | 11/2002 | Jarman et al. |
| 6,494,079 B1 | 12/2002 | Matsiev et al. |
| 6,523,392 B2 | 2/2003 | Porter et al. |
| 6,530,266 B1 | 3/2003 | Adderton et al. |
| 6,535,822 B1 | 3/2003 | Mansky et al. |
| 6,535,824 B1 | 3/2003 | Mansky et al. |
| 6,545,495 B2 | 4/2003 | Warmack et al. |
| 6,575,020 B1 | 6/2003 | de Charmoy Grey et al. |
| 6,598,459 B1 | 7/2003 | Fu |
| 6,606,567 B2 | 8/2003 | Grate et al. |
| 6,650,102 B2 | 11/2003 | Hajduk et al. |
| 6,668,627 B2 | 12/2003 | Lange et al. |
| 6,672,144 B2 | 1/2004 | Adderton et al. |
| 6,763,705 B1 | 7/2004 | Thundat et al. |
| 6,810,720 B2 | 11/2004 | Adderton et al. |
| 6,811,133 B2 | 11/2004 | Miles |
| 6,815,866 B2 | 11/2004 | Lee |
| 6,823,717 B2 | 11/2004 | Porter et al. |
| 6,854,317 B2 | 2/2005 | Porter et al. |
| 6,866,819 B1 | 3/2005 | Chandra et al. |
| 6,904,786 B2 | 6/2005 | Matsiev et al. |
| 6,928,877 B2 | 8/2005 | Carlson et al. |
| 6,935,165 B2 | 8/2005 | Bashir et al. |
| 6,953,977 B2 | 10/2005 | Mlcak et al. |
| 6,955,787 B1 | 10/2005 | Hanson |
| 6,957,565 B2 | 10/2005 | Matsiev et al. |
| 7,260,980 B2 | 8/2007 | Adams et al. |
| 7,521,257 B2 | 4/2009 | Adams et al. |
| 7,694,346 B2 | 4/2010 | Adams et al. |
| 2001/0000279 A1 | 4/2001 | Daniels et al. |
| 2001/0029774 A1 | 10/2001 | Grate et al. |
| 2002/0032531 A1 | 3/2002 | Mansky et al. |
| 2002/0062684 A1 | 5/2002 | Adderton et al. |
| 2002/0092359 A1 | 7/2002 | Lange et al. |
| 2002/0178787 A1 | 12/2002 | Matsiev et al. |
| 2003/0000291 A1 | 1/2003 | Kolosov et al. |
| 2003/0032293 A1* | 2/2003 | Kim et al. .................. 438/694 |
| 2003/0041653 A1 | 3/2003 | Matsiev et al. |
| 2003/0041676 A1 | 3/2003 | Hajduk et al. |
| 2003/0089182 A1 | 5/2003 | Thaysen et al. |
| 2003/0101006 A1 | 5/2003 | Mansky et al. |
| 2003/0154771 A1 | 8/2003 | de Charmoy Grey et al. |
| 2003/0166039 A1 | 9/2003 | Hubler et al. |
| 2003/0218467 A1 | 11/2003 | Carlson et al. |
| 2004/0074303 A1 | 4/2004 | Matsiev et al. |
| 2004/0099050 A1 | 5/2004 | Matsiev et al. |
| 2004/0244487 A1 | 12/2004 | Kolosov et al. |
| 2004/0250622 A1 | 12/2004 | Kolosov et al. |
| 2004/0255651 A1 | 12/2004 | Adderton et al. |
| 2005/0009197 A1 | 1/2005 | Adams et al. |
| 2005/0016276 A1 | 1/2005 | Guan et al. |
| 2005/0034542 A1 | 2/2005 | Thaysen |
| 2005/0066714 A1 | 3/2005 | Adderton et al. |
| 2005/0133877 A1 | 6/2005 | Thaysen et al. |
| 2005/0164299 A1 | 7/2005 | Stewart |
| 2005/0166679 A1 | 8/2005 | Carlson et al. |
| 2005/0199047 A1 | 9/2005 | Adams et al. |
| 2005/0229713 A1 | 10/2005 | Niblock |
| 2006/0032289 A1 | 2/2006 | Pinnaduwage et al. |
| 2006/0257286 A1 | 11/2006 | Adams et al. |
| 2006/0257296 A1 | 11/2006 | Lipp |
| 2009/0229020 A1 | 9/2009 | Adams et al. |
| 2010/0288015 A1 | 11/2010 | Adams et al. |

FOREIGN PATENT DOCUMENTS

| | | |
|---|---|---|
| WO | WO00/20850 A1 | 4/2000 |
| WO | WO03/044530 A1 | 5/2003 |
| WO | WO03/062135 A1 | 7/2003 |
| WO | WO03/067248 A1 | 8/2003 |
| WO | WO03/071258 A1 | 8/2003 |
| WO | WO03/095616 A2 | 11/2003 |
| WO | WO03/104784 A1 | 12/2003 |
| WO | WO2004/059306 A1 | 7/2004 |
| WO | WO2004/083802 A2 | 9/2004 |
| WO | WO2005/029042 A2 | 3/2005 |
| WO | WO2005/083409 A1 | 9/2005 |
| WO | WO2006/039506 A3 | 4/2006 |

OTHER PUBLICATIONS

Adams, et al., "Taking Atomic Force Microscopy Advances to the University Classroom," Aerospace Conference, 2001, IEEE Proceedings Mar. 10, 2001-Mar. 17, 2011 7:7-3673-7-3682 (2001).

Barrettino, et al., "CMOS Monolithic Mechatronic Microsystem for Surface Imaging and Force Response Studies," IEEE Journal of Solid-State Circuits 40(4):951-959 (Apr. 2005).

Binnig, et al., "Ultrahigh-density Atomic Force Microscopy Data Storage With Erase Capability," Applied Physics Letters 74(9):1329-1331 (Mar. 1, 1999).

Bustillo, et al., "Surface Micromachining for Microelectromechanical Systems," Proceedings of the IEEE 86 (8):1552-1574 (Aug. 1998).
Itoh, et al., "Piezoelectric Cantilever Array for Multiprobe Scanning Force Microscopy," Micro Electro Mechanical Systems, 1996, MEMS '96, Proceedings. 'An Investigation of Micro Structures, Sensors, Actuators, Machines and Systems'. IEEE, The Ninth Annual International Workshop on 451-455 (Feb. 11, 1996).
Liu, et al., "On the Modes and Loss Mechanisms of a High Q Mechanical Oscillator," Applied Physics Letters 78 (10):1346-1348 (Mar. 5, 2001).
Mathieu, et al., "Piezoresistive Signal Down Mixing for Parallel Detection of Si-based Microcantilevers Resonant Frequencies," Sensors, 2005 IEEE 708-711 (Oct. 30, 2005).
Minne, et al., "Parallel Atomic Force Microscopy Using Cantilevers With Integrated Piezoresistive Sensors and Integrated Piezoelectric Actuators," Applied Physics Letters 67(26):3918-3920 (Dec. 25, 1995).
Omote, et al., "Temperature Dependence of Elastic, Dielectric, and Piezoelectric Properties of 'Single Crystalline' Films of Vinylidene Fluoride Trifluoroethylene Copolymer," Journal of Applied Physics 81(6):2760-2769 (Mar. 15, 1997).
Savran, et al., "Fabrication and Characterization of a Micromechanical Sensor for Differential Detection of Nanoscale Mofions," Journal of Microelectromechanical Systems 11(6):703-708 (Dec. 2002).
Tortonese, et al., "Characterization of Application Specific Probes for SPMs," Proceedings SPIE 3009:53-60 (Apr. 1997).
Wolf, et al., "Temperature Dependence of the Piezoelectric Response in Lead Zirconate Titanate Films," Journal of Applied Physics 95(3):1397-1406 (Feb. 1, 2004).
Yasumura, et al., "Quality Factors in Micron- and Submicron-Thick Cantilevers," Journal of Microelectricalmechanical Systems 9(1):117-125 (Mar. 2000).
Yazdi, et al., "Micromachined Inertial Sensors," Proceedings of the IEEE 86(8):1640-1659 (Aug. 1998).
Abedinov, et al., "Micromachined Piezoresistive Cantilever Array with Integrated Resistive Microheater for Calorimetry and Mass Detection," Journal of Vacuum & Science Technology 19(6); pp. 2884-2888 (Nov./Dec. 2001).
Adams, "Scanning Probe Microscope Development, MEMS, and Nanotechnology,", Nevada Ventures in Nanoscience Program Presentation; pp. 1-27 (Aug. 12, 2002).
Adams, et al., "Nanowatt Chemical Vapor Detection With a Self-Sensing, Piezoelectric Microcantilever Array," Applied Physics Letters, vol. 83, No. 16, pp. 3428-3430 (Oct. 20, 2003).
Ali, et al. , "Organic Vapour Sensing Using a Coated Piezoelectric Quartz Crystal Sensor Array," SPIE 3853; pp. 116-120 (Sep. 1999).
Alper, "Chemical Engineering at the Nanoscale," NCI Alliance for Nanotechnology in Cancer; pp. 1-4 (May 2005).
Baborowski, "Microfabrication of Piezoelectric MEMS," Swiss Center for Electronics and Microtechnology; pp. 1-55 (Oct. 7-8, 2004).
Barko, et al., "Application of Fuzzy Clustering and Piezoelectric Chemical Sensor Array for Investigation on Organic Compounds," Analytica Chemica Acta 398:219-226 (1999).
Barnes, et al., "A Femtojoule Calorimeter Using Micromechanical Sensors," Rev. Sci. Instrum, vol. 65, No. 12:3793-3798 (Dec. 1994).
Baselt et al., "Biosensor Based on Force Microscope Technology," J. Vac .Sci. Technol. B 14(2):789-793, (Mar./Apr. 1996).
Battiston et al., "A Chemical Sensor Based on a Microfabricated Cantilever array With Simultaneous Resonance-frequency and Bending Readout," Sensors and Actuators B, 77:122-131 (2001).
Berger, et al., "Micromechanical Thermogravimetry," Chemical Physics Letters, vol. 294:363-369 (Sep. 18, 1998).
Berger, et al., "Micromechanics: A Toolbox for Femtoscale Science: Towards a Laboratory on a Tip," Microelectronic Engineering, vol. 35:373 (1997).
Berger et al., "Transduction Principles and Integration of Chemical Sensors into a Micromechanical Array Device," IBM Research Division Research Report, (Dec. 1997).
Blick et al., "Nanostructured Silicon for Studying Fundamental Aspects of Nanomechanics," Journal of Physics CM 14:R905-R945 (2002).

Braun et al., "Micromechanical Mass Sensors for Biomolecular Detection in a Physiological Environment," Physical Review 72(3):031907(9) (2005).
Britton, C.L. Jr. et al, "Multiple-Input Microcantilever Sensors" Ultramicroscopy 82, pp. 17-21 (2000).
Bruckner et al., "Piezoelektrisch Gekoppelte Integrierbare Nanoelektromechannische Sensorschaltungen" Integrierte elllekktrokeramische Funktionsstrukkturen; pp. 1-20, (Sep. 28-29, 2004).
Burg et al., "Suspended Microchannel Resonators for Biomolecular Detection," Applied Physics Letters 83(13):2698-2700 (Sep. 29, 2003).
Campbell et al., "Detection and Quantification of Proteins Using Self-Excited PZT-Glass Millimeter-Sized Cantilever," Biosensors and Bioelectronics 21:597-607 (Jan. 22, 2005).
Cavicchi, et al., "Micro-differential scanning calorimeter for combustible gas sensing," Sensors and Actuators, vol. B 97, pp. 22-30 (2004).
Chen et al., "Resonance Response of Scanning Force Microscopy Cantilevers," Rev. Sci. Instrum. 65(8): 2532-2537 (Aug. 1994).
Chen et al., "Adsorption-Induced Surface Stress and its Effects on Resonance Frequency of Microcantilevers," J. Appl. Phys. 77(8):3618-3622 (Apr. 15, 1995).
Cherian et al., "Determination of Adsorption-Induced Variation in the Spring Constant of a Microcantilever," Applied Physics Letters 80 (12):2219-2221 (Mar. 25, 2002).
Chu et al., "Novel High Vacuum Scanning Force Microscope Using a Piezoelectric Cantilever and the Phase Detection Method," J. Vac .Sci. Technol. B 15(4):1551-1555 (Jul./Aug. 1997).
Chu et al., "Frequency Modulation Detection High Vacuum Scanning Force Microscope With a Self-Oscillating Piezoelectric Cantilever," J. Vac. Sci. Technol. B 15(5):1647-1651 (Sep./Oct. 1997).
Chu et al., "Tip-Scanning Dynamic Force Microscope Using Piezoelectric Cantilever for Full Wafer Inspection," Jpn .J. Appl. Phys. 38(Part 1, No. 123):7155-7158 (Dec. 1999).
Datskos, et al., "Chemical Sensors Based on Nanomechanical Resonators," CalSpec factsheet, OakRidge National Laboratory.
Datskos, et al., "Micro and Nanocantilever Sensors," Encyclopedia of Nanoscience and Nanotechnology X; pp. 1-10 (2004).
Datskos, et al., "Detection of Chemical, Biological and Radiological Stimuli Using Nanosensor Arrays," CalSpec factsheet, OakRidge National Laboratory.
Datskos, et al., "MEMS Based Calorimetric Spectroscopy," CalSpec factsheet, OakRidge National Laboratory.
Datskos, et al., "Nanocantilever Signal Transduction by Electron Transfer," Journal of Nanoscience and Nanotechnology, vol. 2., No. 3/4: pp. 369-373 (2002).
Davis, et al., "Fabrication and Characterization of Nanoresonating Devices for Mass Detection," Journal of Vacuum & Science Technology, 18(2); pp. 612-616 (Mar./Apr. 2000).
DeVoe, et al., "Modeling and Optimal Design of Piezoelectric Cantilever Microactuators," JMEMS, vol. 6(3): pp. 266-270 (Sep. 1997).
DeVoe, "Piezoelectric Thin Film Micromechanical Beam Resonators," Sensors and Actuators A(88):263-272, (2001).
DeVoe, "Thin Film Zinc Oxide Microsensors and Microactuators," Ph.D. Dissertation, University of California, Berkeley (1997).
Dohn et al., "Enhanced Functionality of Cantilever Based Mass Using Higher Modes," Applied Physics Letters 86:233501-3 (Jun. 3, 2005).
Ekinci, "Ultimate Limits to Inertial Mass Sensing Based Upon Nanoelectromechanical Systems," Journal of Applied Physics 95(5):2682-2689 (Mar. 1, 2004).
Ekinci et al, "Nanoelectromechanical Systems," Review of Scientific Instruments 76:061101-1 (May 26, 2005).
Fabian, et al., "Micromechanical Thermograimetry on Single Zeolite Crystals," IBM Research Report, vol. RZ 3047, (93093) 4 pages (Aug. 17, 1998).
Fadel et al., "Signal-to-Noise Ratio of Resonant Microcantilever Type Chemical Sensors as a Function of Resonant Frequency and Quality Factor," Sensors and Actuators B 102:73-77 (Jan. 23, 2004).
Fannin, "Design of an Analog Adaptive Piezoelectric Sensoriactuator," MS Thesis Virginia Polytechnic Institute and State University 1-81 (Feb. 26, 1997).

Ferrari, et al., "Resonant Piezo-Layers in Thick Film Technology Applied to Gravimetric Chemical Sensing," *Sensors and Microsystems: Proceedings of the First National Conference on Sensors and Microsystems AISEM*, Roma, World Scientific Publishing, Singapore, 256-260 (Feb. 19-20, 1996).

Foerster, et al., "Processing of Novel SiC and group III-Nitride Based Micro and Nanomechanical Devices," *Phys. Stat. Sol. A* 202(4):671-676 (2005).

Forster et al., "Project π-NEMS, DFG-SPP 1157," *Präsentation Status Meeting*, (2004).

Fon et al., "Nanoscale, Phonon-Coupled Calorimetry with Sub-Attojoule/Kelvin Resolution," *Nano Letters* 5(10):1968-1971 (2005).

Fujii et al., "Feedback Positioning Cantilever Using Lead Zirconate Titanate Thin Film for Force Microscopy Observation of Micropattern," *Applied Physics Letters* 68(4):467-468 (Jan. 22, 1996).

Guan, S., "Frequency Encoding of Resonant Mass Sensors for Chemical Vapor Detection" *Analytical Chemistry*, 75 (17), pp. 4551-4557 (Jul. 17, 2003).

Horowitz et al., "Design and Characterization of a Micromachined Piezoelectric Microphone," *11th AIAA/CEAS Aeroacoustics Conference* 2005 (May 23-25, 2005), 1-10.

Huang et al., "VHF/UHF and Microwave Frequency Nanomechanical Resonators," *New Journal of Physics* 7 (247):1-15, (Nov. 29, 2005).

Hughes, "A Microfabricated Piezoelectric Cantilever Beam Biosensor," *Ph.D. Dissertation University of Minnesota*, (Aug. 1999).

Indermuhle et al., "Self-Sharpening Tip Integrated on Micro Cantilevers With Self-Exciting Piezoelectric Sensor for Parallel Atomic Force Microscopy," *Applied Physics Letters* 70(17):2318-2320 (Apr. 28, 1997).

Itoh et al., "Development of a Force Sensor for Atomic Force Microscopy Using Piezoelectric Thin Films," *Nanotechnology* 4:218-224 (1993).

Itoh et al., "Force Sensing Microcantilever Using Sputtered Zinc Oxide Thin Film," *Appl. Phys. Lett.* 64(1):37-39 (Jan. 3, 1994).

Itoh et al., "Deflection Detection and Feedback Actuation Using a Self-Excited Piezoelectric Pb(Zr,Ti)O$_3$ Microcantilever for Dynamic Scanning Force Microscopy," *Applied Physics Letters* 69(14):2036-2038 (Sep. 30, 1996).

Itoh et al., "Self-Excited Force-Sensing Microcantilevers with Piezoelectric Thin Films for Dynamic Scanning Force Microscopy," *Sensors and Actuators A* 54:477-481 (1996).

Itoh et al., "Piezoelectric Sensor for Detecting Force Gradients in Atomic Force Microscopy," *Jpn. J. Appl. Phys.* 33(Part 1, 1A):334-340 (Jan. 2004).

Jain et al., "A Microheater Device for Study of Temperature Gradient Effects on Neurite Outgrowth in Retinal Ganglion Cells," *ARVO Annual Meeting 2004*, Ft. Lauderdale, FL, (Apr. 25-28, 2004).

Johnson, "Characterization of Piezoelectric ZnO Thin Films and the Fabrication of Piezoelectric Micro-Cantilevers" *Thesis, Iowa State University*; pp. 1-98 (2005).

Kim et al., "Multicomponent Analysis and Prediction with a Cantilever Array Based Gas Sensor," *Sensor and Actuators B* 78:12-18 (2001).

Lange, et al., "Complimentary Metal Oxide Semiconductor Cantilever Arrays on a Single Chip: Mass-Sensitive Detection of Volatile Organic Compounds," *Anal. Chem.* 74 (13):3084-3095 (Jul. 1, 2002).

Lang, et al. "Nanomechanics from Atomic Resolution to Molecular Recognition Based on Atomic Force Microscopy Technology," *Nanotechnology* 13: R29-R36 (Sep. 25, 2002).

Lange, D. et al, "CMOS Resonant Beam Gas Sensing System With On-Chip Self Excitation", *IEEE International Conference on Micro Electro Mechanical Systems*, Technical Digest (14) 547-552, (Jan. 21-25, 2001).

Lang et al., "The Nanomechanical NOSE," *Chem. Phys. Lett.* 217:589-594 (1994).

Lavrik, et al., "Cantilever Transducers as a Platform for Chemical and Biological Sensors," *Review of Scientific Instruments*, vol. 75, (7); pp. 2229-2253 (Jan. 2004).

Lee, C. et al, Technical Digest—International Electron Devices Meeting, 545-548 (1996).

Lee, et al., "Microcantilevers Integrated With Heaters and Piezoelectric Detectors for Nano Data-Storage Application," *Applied Physics Letters*, 83, (23), 4839-4841 (Dec. 8, 2003).

Lee, et al., "Self-Excited Piezoelectric Cantilever Oscillators," *Sensors and Actuators*, A 52, 41-45 (1996).

Lee et al., "Characterization of Micromachined Piezoelectric PZT Force Sensors for Dynamic Scanning Force Microscopy," *Rev. Sci. Instrum.* 68(5):2091-2100 (May 1997).

Lee et al., "Development of a Piezoelectric Self-Excitation and Self-Detection Mechanism in PZT Microcantilevers for Dynamic Scanning Force Microscopy in Liquid," *J. Vac. Sci. Technol. B* 15(4):1559-1563 (Jul./Aug. 1997).

Lee et al., "Piezoelectric Cantilever Acoustic Transducer," *J. Micromech. Microeng.* 8:230-238 (1998).

Lee et al., "Self-Excited Piezoelectric PZT Microcantilevers for Dynamic Sfm-with Inherent Sensing and Actuating Capabilities," *Sensors and Actuators A* 72:179-188 (1999).

Li et al., "Electromechanical Behavior of PZT-Brass Unimorphs," *J. Am. Ceram. Soc.* 82(7):1733-1740 (1999).

Madden et al., "Conducting Polymer Sensors for the Home," Publication Source and Publication Date Unknown.

Manning, et al., "Self-Oscillating Tapping Mode Atomic Force Microscopy," *Review of Scientific Instruments*, 74 (9): 4220-4222 (Sep. 2003).

Marie, R. et al, "Adsorption Kinetics and Mechanical Properties of Thiol-Modified DNA-Oligos on Gold Investigated by Microcantilever Sensors" Ultramicroscopy, 91, 29-36 (2002).

Martin et al., "Isothermal Measurements and Thermal Desorption of Organic Vapors Using SAW Devices," *IEEE Transactions on Ultrasonics, Ferroelectrics, and Frequency Control* 34(2):142-147 (Mar. 1987).

Mehta et al., "Manipulation and Controlled Amplification of Brownian Motion of Microcantilever Sensors," *Applied Physics Letters* 78(11):1637-1639 (Mar. 12, 2001).

Miller et al., "A MEMS Radio-Frequency Ion Mobility Spectrometer for Chemical Agent Detection (abstract)," *Proceedings of the 2000 Solid-State Sensor and Actuator Workshop*, Hilton Head Island, SC 36-43 (Jun. 4-8, 2000).

Minne et al., "Contact imaging in the Atomic Force Microscope Using a Higher Order Flexural Mode Combined With a New Sensor," *Applied Physics Letters* 68(10):1427-1429 (Mar. 4, 1996).

Miyahara et al., "Lead Zirconate Titanate Cantilever for Noncontact Atomic Force Microscopy," *Applied Surface Science* 140:428-431 (1999).

Miyahara et al., "Non-Contact Atomic Force Microscope with a PZT Cantilever Used for Deflection Sensing, Direct Oscillation and Feedback Actuation," *Applied Surface Science* 188:450-455 (2002).

Moriizumi, T. et al, "Multi-Channel Saw Chemical Sensor Using 90Mhz Saw Resonator and Partial Casting Molecular Films" Proceedings—IEEE Ultrasonics Symposium, 449-502 (1994).

Muralidharan et al., "Absorption-Desorption of Explosive Vapors Investigated With Microcantilevers," *Ultramicroscopy* 97:433-439 (2003).

Nam, et al., "Piezoelectric PZT Cantilever Array Integrated with Piezoresistor for High Speed Operation and Calibration of Atomic Force Microscopy," *Journal of Semiconductor Technology and Science*, 2 (4): 246-252 (Dec. 2002).

Nam et al., "End Point Motion Estimation of a Cantilevered Piezoelectric Beam," *International Conference on Mechatronics and Information Technology*, Japan 215-219, (2001).

Oden, "Gravimetric Sensing of Metallic Deposits Using an End-Loaded Microfabricated Beam Structure," *Sensors and Actuators B* 53:191-196 (1998).

Paci et al., "A Behavioural Model of Resonant Cantilevers for Chemical Sensing," *Analog Integrated Circuits and Signal Processing* 44:119-128 (2005).

Passian et al., "Dynamics of Self-Driven Microcantilevers," *Journal of Applied Physics* 91(7):4693-4700 (Apr. 1, 2002).

Piekaraski et al., "Surface Micromachined Piezoelectric Resonant Beam Filters," *Sensors and Actuators* A 90(3):313-20 (2001).

Pinnaduwage, et al., "A Microsensor for Trinitrotoluene Vapour," *Nature*, 425: 474 (Oct. 2, 2003).

Pinnaduwage et al., "Adsorption of Trinitrotoluene on Uncoated Silicon Microcantilever Surfaces," *Langmuir* 20 (7):2690-2694 (2004).

Pinnaduwage et al., "Detection of 2, 4-Dinitrotoluene Using Microcantilever Sensors," *Sensors and Actuators B* 1-72 (2004).

Pinnaduwage et al., "Moore's Law in Homeland Defense—An Integrated Sensor Platform Based on Silicon Microcantilevers," *IEEE Sensors Journal* 5(4):774-785 (Aug. 2005).

Polla et al., "Processing and Characterization of Piezoelectric Materials and Integration into Microelectromechanical Systems," *Annu. Rev. Mater. Sci.* 28:563-597 (1998).

Polla, et al., "Integrated Multi-Sensor Chip," *IEEE Electron Device Letters* EDL-7 (4): 254-256 (Apr. 1986).

Porter, T.L. et al, "Sensor Based on Piezoresistive Microcantilever Technology" *Sensors and Actuators* A, 88, 47-51 (2001).

Postma et al., "Dynamic Range of Nanotube- and Nanowire-Based Electromechanical Systems," *Applied Physics Letters* 86:223105-3 (May 25, 2005).

Pozidis et al., "Demonstration of Thermomechanical Recording at 641 Gbit/in$^2$," *IEEE Transactions on Magnetics* 40(4):2531-2536 (Jul. 2004).

Rogers, et al., "Mercury Vapor Detection with a Self-Sensing, Resonating Piezoelectric Cantilever," *Review of Scientific Instruments*, 74(11): 4899-4901 (Nov. 2003).

Rogers et al., "Improving Tapping Mode Atomic Force Microscopy with Piezoelectric Cantilevers," *Ultramicroscopy* 100:267-276 (2004).

Ruby "FBAR-From Technology Development to Production," *Second International Symposium on Acoustic Wave Devices for Future Mobile Communications Systems*, (Mar. 2005).

Semanick et al., "Microhotplate Platforms for Chemical Sensor Research," *Sensors and Actuators B* 77:579-591 (2001).

Sharos et al., "Enhanced Mass Sensing Using Torsional and Lateral Resonances in Microcantilevers," *Applied Physics Letters* 84(23):4638-4640 (Jun. 7, 2004).

Shibata et al., "Characterization of Sputtered ZnO Thin Film as Sensor and Actuator for Diamond AFM Probe," *Sensors and Actuators A* 102:106-113 (2002).

Shih et al., "Simultaneous Liquid Viscosity Density Determination with Piezoelectric Unimorph Cantilevers," *Journal of Applied Physics* 89(2):1497-1505 (Jan. 15, 2001).

Shin, et al. "Fabrication and Sensing Behavior of Piezoelectric Microcantilever for Nanobalance," *Japanese Journal of Applied Physics* 42 (Part 1 No. 9B): 6139-6142 (2003).

Su et al., "Microcantilever Resonance-Based DNA Detection with Nanoparticle Probes," *Applied Physics Letters* 82(20):3562-3564 (May 19, 2003).

Suehira et al., "Development of Low Temperature Ultrahigh Vacuum Noncontact Atomic Force Microscope with PZT Cantilever," *Applied Surface Science* 157:343-348 (2000).

Sulchek, et al., "Dual Integrated Actuators for Extended Range High Speed Atomic Force Microscopy," *Applied Physics Letters*, 75 (11): 1637-1639 (Sep. 13, 1999).

Tamayo et al., "Chemical Sensors and Biosensors in Liquid Environment Based on Microcantilevers with Amplified Quality Factor," *Ultramicroscopy* 0:1-7 (2001).

Tani et al., "Effectiveness and Limits of Self-Sensing Piezoelectric Actuators" *International Workshop on Structural Health Monitoring Stanford University* 502-514 (Sep. 18-20, 1997).

Tatsuma, T. et al, "Multichannel Quartz Crystal Microbalance" *Analytical Chemistry*, 71 (17): 3632-3636 (Sep. 1999).

Thundat et al., "Thermal and Ambient-Induced Deflections of Scanning Force Microscope Cantilevers," *Appl. Phys. Lett.* 64(21):2894-2896 (May 23, 1994).

Thundat et al., "Detection of Mercury Vapor Using Resonating Microcantilevers," *Applied Physics Letters* 66(13):1695-1697 (Mar. 27, 1995).

Voiculescu et al., "Electrostatically Actuated Resonant Microcantilever Beam in CMOS Technology for the Detection of Chemical Weapons," *IEEE Sensors Journal* 5(4):641-647 (Aug. 2005).

Wang et al., "Theoretical Analysis of the Sensor Effect of Cantilever Piezoelectric Benders," *Journal of Applied Physics* 85(3):1702-1712 (Feb. 1, 1999).

Watanabe et al., "Micro-Fabricated Piezoelectric Cantilever for Atomic Force Microscopy," *Rev .Sci. Instrum.* 67(11):3898-3903 (Nov. 1996).

Weigert et al., "Frequency Shifts of Cantilevers Vibrating in Various Media," *Applied Physics Letters* 69(19):2834-2836 (Nov. 4, 1996).

Weinberg, "Working Equations for Piezoelectric Actuators and Sensors," *ASME/IEEE Journal of MEMS* 8(4):71-78 (1999).

Wright, "Fabrication and Testing of Heated Atomic Force Microscope Cantilevers," *Georgia Institute of Technology Thesis* 1-111 (May 2005).

Yang et al., "Mechanical Behavior of Ultrathin Microcantilever," *Sensors and Actuators* 82:102-107, 2000.

Yi, et al., "In Situ Cell Detection Using Piezoelectric Lead Zirconate Titanate-Stainless Steel Cantilevers," *J. Applied Physics* 93 (1): 619-625 (Jan. 1, 2003).

Yi, et al., "Effect of Length, Width, and Mode on the Mass Detection Sensitivity of Piezoelectric Unimorph Cantilevers," *J. Applied Physics* 91 (3): 1680-1686 (Feb. 1, 2002).

Yue et al., "Cantilever Arrays for Multiplexed Mechanical Analysis of Biomolecular Reactions," *MCB* 1(3):211-220 (2004).

Zhang et al., "Tuning Forks as Micromechanical Mass Sensitive Sensors for Bio- or Liquid Detection," *Sensors and Actuators B* 94:65-72 (2003).

Zhang et al., "Frequency-Tuning for Control of Parametrically Resonant Mass Sensors," *J. Vac. Sci .Technol. A* 23(4):1-5 (Jul./Aug. 2005).

Zhou, J. et al, "Self-Excited Piezoelectric Microcantilever for Gas Detection" *Microelectronic Engineering*, 69, 37-46 (2003).

\* cited by examiner

SELF-SENSING ARRAY OF MICROCANTILEVERS FOR CHEMICAL DETECTION

CROSS-REFERENCE TO RELATED APPLICATIONS

This application is a Continuation of U.S. patent application Ser. No. 11/845,680, filed Aug. 27, 2007 (pending), which is a Continuation of U.S. patent application Ser. No. 10/967,748, filed Oct. 15, 2004 (abandoned), which in turn claims the benefit of U.S. Provisional Application No. 60/512,504, filed Oct. 17, 2003. This application is related to U.S. Ser. No. 11/845,661, filed Aug. 27, 2007, U.S. Ser. No. 12/416,852, filed Apr. 1, 2009, and U.S. Ser. No. 12/748,788, filed Mar. 29, 2010.

FIELD OF THE INVENTION

This invention relates generally to chemical-sensing methods, and in particular, relates to a method and system for sensing specific chemicals and biological materials using an array of piezoelectrically driven cantilevered probes with selectively disposed chemical sensitive coatings.

BACKGROUND OF THE INVENTION

Micromachined cantilevers are used in atomic force microscopy (AFM) for surface scanning and for chemical, biological, and other sensing applications. Micromachined cantilevers may become the basis for specialized, ultraminiature, ultrasensitive sensors for detection of specific target chemical species such as chemical compounds, bioactive agents, or toxins. Miniaturized chemical sensors hold promise for applications needing sensitive chemical detection, quality control of materials processing, and measurements of small or limited quantities of a chemical or biological material. Resonance-based detection has been demonstrated specifically for sensing mercury vapor, ultraviolet radiation, relative humidity, magnetic susceptibility, and sub-nanogram masses.

AFM is a method of measuring surface topography on a scale typically from a few angstroms or less to a hundred micrometers or more. The technique involves imaging a sample through the use of a probe or tip suspended from one end of a microcantilever. A surface is probed with the tip, and the interaction between the tip and sample is measured. Physical topography, surface chemistry, charge density, magnetic properties, local temperature and other surface properties can be analyzed.

Lasers can be used for optical detection of cantilever movement, though AFM systems using lasers require comparably high power on the order of milliwatts, need alignment, have limited resolution, and are prone to drift because of the size of the optical path. Current systems typically require external lighting for sample illumination and setup, and are not very compact because of the long optical path, the need to have the photodetector at an ample distance from the sample, and constrained viewing and positioning systems for optical alignment. Sample testing in liquids such as water or saline solution presents additional difficulties for optical sensing due to aberrations and refraction of the light beam traversing the fluid.

Lasers have been used to detect frequency changes of a microcantilever that is oscillated by a piezoelectric transducer, as taught in "Microbar Sensor," Wachter et al., U.S. Pat. No. 5,445,008 issued Aug. 29, 1995. Oscillation frequency changes are detected by a center-crossing photodiode that responds to a laser diode beam reflected from the microcantilever surface resulting in an output frequency from the photodiode that is synchronous with the microcantilever frequency.

AFM systems using microcantilevers and laser detection have been used for analyzing explosive gas molecules adsorbed onto the microcantilevers, as described in "Microcantilever Detector for Explosives," Thundat, U.S. Pat. No. 5,918,263 issued Jun. 29, 1999. Analysis can be made of the laser beam reflected by the heat-induced deflection and transient resonant response of the microcantilever.

Because power efficiency is important to the size, lifetime, and utility of a cantilever sensor, alternative detection schemes to those using lasers have been proposed. Notably, capacitive systems are being developed to monitor cantilever deflection. While a low-power option, capacitive cantilever sensing is most suitable under vacuum conditions to avoid excessive air damping between the two electrodes of the capacitor. Other limitations of capacitive schemes include small tolerances for fabrication and coatings of a cantilever, a reliance on a small sensing gap size, and difficulties with sensing in liquid solutions.

In an alternative sensing scheme to optical detection or capacitive sensing, AFM systems in a vibrating or tapping mode may use actuated piezoresistive cantilevers. Piezoresistive sense methods are more compact than optical systems, though they can self-heat and cause drift. Furthermore, piezoresistive sensing typically consumes large portions of available power when used in a portable device. A typical piezoresistive cantilever, which also can use milliwatts of power, is a micro-electrical-mechanical-system (MEMS) device, micromachined from bulk silicon with a piezoelectric film patterned along a portion of the microcantilever. At the free end of the cantilever is a tip with nanometer-scale radius, optimally shaped to probe the sample surface. The microcantilever is displaced by voltage applied to the piezoelectric actuator, resulting in a controlled vertical movement of the tip. Control electronics drive the microcantilever while simultaneously positioning it vertically to track the sample topography and follow the surface features. A macro-scale position actuator may be used to null the position of the cantilever, following the topology of the sample as the probe is scanned over the surface.

Chemicals can be sensed based on frequency shifts of microcantilevers treated with a compound-selective substance, as disclosed in "Microcantilever Sensor," Thundat et al., U.S. Pat. No. 5,719,324 issued Feb. 17, 1998. A microsensor with a cantilever attached to a piezoelectric transducer is capable of detecting changes in the resonance frequency and the bending of the vibrated cantilever in a monitored atmosphere. Upon insertion into a monitored atmosphere, molecules of a targeted chemical to be sensed attach to the treated regions of the microcantilever resulting in a change in oscillating mass as well as a change in microcantilever spring constant thereby influencing the resonant frequency of the microcantilever oscillation.

Oscillating silicon nitride cantilevered beams coated with a thin gold film have been used to detect mercury vapor in air due to changes in cantilever resonant frequency and stress levels induced in the gold overlayer as described by Thundat, et al., in "Detection of Mercury Vapor Using Resonating Microcantilevers," *Appl. Phys. Lett.* 66 (13), 27 Mar. 1995, pp. 1695-1697. An uncoated microcantilever can be used for chemical sensing by exciting charge carriers into or out of surface states with discrete photon wavelengths as disclosed by Thundat, et al., in "Uncoated Microcantilevers as Chemical Sensors," U.S. Pat. No. 6,212,939, issued Apr. 10, 2001. Attempts at DNA sequencing and detection using an AFM is described by Allen in "Method and Apparatus for DNA Sequencing Using a Local Sensitive Force Detector," U.S. Pat. No. 6,280,939, issued Aug. 28, 2001.

An exemplary cantilever with a piezoelectric drive and a piezoresistive sense is disclosed in "Atomic Force Microscope for High Speed Imaging Including Integral Actuator and Sensor," Minne et al., U.S. Pat. No. 5,883,705 issued Mar. 16, 1999, and "Cantilever for Scanning Probe Microscope Including Piezoelectric Element and Method of Using the Same," Minne et al., U.S. Pat. No. 5,742,377 issued Apr. 21, 1998. When the scanning probe microscope (SPM) operates in the constant force mode, the piezoelectric element is used to control the tip-sample separation. Since the resonant frequency of the piezoelectric element is substantially higher than that of conventional piezoelectric tube scanners, much higher scan rates can be achieved. When the SPM operates in the dynamic or intermittent contact mode, a superimposed AC-DC signal is applied to the piezoelectric element, and the latter is used to vibrate the cantilever as well as to control the tip-sample spacing.

Piezoelectrically driven cantilevers have been proposed to eliminate the need for external actuators. An exemplary self-actuating cantilever is described in "Active Probe for an Atomic Force Microscope and Method of Use Thereof," Adderton et al., U.S. Pat. No. 6,530,266 issued Mar. 11, 2003 and "Atomic Force Microscope for High Speed Imaging Including Integral Actuator and Sensor," Adderton et al., U.S. Pat. No. 6,189,374 issued Feb. 20, 2001. This system includes a self-actuated cantilever having a Z-positioning element integrated therewith and an oscillator that oscillates the self-actuated cantilever at a frequency generally equal to a resonant frequency of the self-actuated cantilever.

In response to the growing interest in using cantilevers for chemical sensing, researchers are developing systems with multiple cantilever sensors or modular sensor array systems to characterize larger numbers of material samples more quickly. An example of an system of multiple cantilevers in a substantially linear configuration that uses individually-selectable cantilevers with a different resonance frequency for each is disclosed in "Multiprobe and Scanning Probe Microscope," Shimizu et al., U.S. Pat. No. 6,469,293 issued Oct. 22, 2002. A modular sensor array system has been suggested for rapid deposition of sample chemicals on sensor arrays in "Sensor Array-Based System and Method for Rapid Materials Characterization," Mansky et al., U.S. Pat. No. 6,535,824, issued Mar. 18, 2003 and "Sensor Array for Rapid Materials Characterization," Mansky et al., U.S. Pat. No. 6,535,822, issued Mar. 18, 2003. One intended goal is to eliminate the need for multiple materials characterization machines and the need for application-specific active circuitry within the sensor arrays themselves.

In light of the discussion above, an improved system for sensing chemicals is desirable that is more compact and power-efficient than piezoresistively or optically sensed AFM cantilevers, does not require off-chip actuation for frequency measurements, does not require individual addressing of each cantilever to determine the natural frequencies, is capable of operating in liquid or gas, and generates less unwanted heat than other AFM cantilever systems. Cantilevers need to be small and light for rapid detection of minute concentrations of target chemicals and biomaterials. Therefore, a desirable method and system for chemical sensing incorporates these improvements and overcomes the deficiencies described above.

SUMMARY OF THE INVENTION

One aspect of the invention provides a chemical detection system for detecting at least one target chemical species. The system includes a self-sensed cantilevered probe array with a plurality of self-sensed cantilevered probes; one or more chemical-sensitive coating materials applied to at least one cantilevered probe in the cantilevered probe array; and an interface circuit coupled to the cantilevered probe array. One or more chemical-sensitive coated cantilevered probes in the cantilevered probe array exhibit a shifted cantilevered probe response when the cantilevered probe array is exposed to the target chemical species and is actuated by the interface circuit.

Another aspect of the invention is a method of chemical detection. A self-sensed cantilevered probe is exposed to a target chemical species and the exposed cantilevered probe array is actuated. A cantilevered probe response from at least one self-sensed cantilevered probe in the cantilevered probe array is detected, and the target chemical species is determined based on the detected cantilevered probe response.

Another aspect of the invention is a handheld system for sensing a target chemical species including an enclosure, a self-sensed cantilevered probe array coupled to the enclosure, at least one chemical-sensitive coating material applied to at least one cantilevered probe in the cantilevered probe array, and an interface circuit coupled to the cantilevered array. The enclosure includes an inlet port for the ingression of the target chemical species and an outlet port for the egression of the target chemical species. The cantilevered probe array includes a plurality of self-sensed cantilevered probes. At least one cantilevered probe in the cantilevered probe array exhibits a shifted cantilevered probe response when the cantilevered probe array is exposed to the target chemical species and is actuated by the interface circuit.

BRIEF DESCRIPTION OF THE DRAWINGS

The current invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings. Various embodiments of the present invention are illustrated by the accompanying figures, wherein:

DETAILED DESCRIPTION OF THE INVENTION

Figure 1:
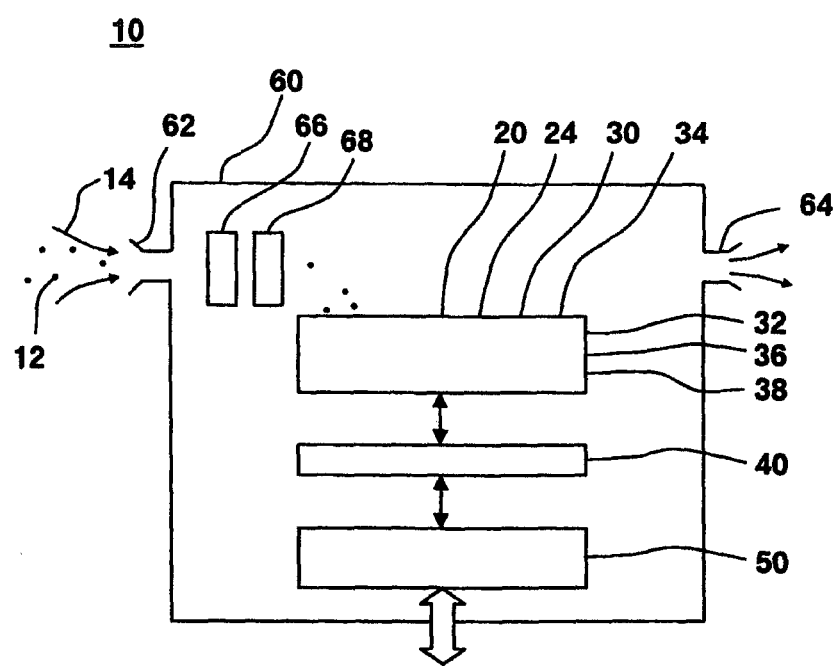
FIG. 1 illustrates a chemical detection system for detecting at least one target chemical species, in accordance with one embodiment of the current invention.

FIG. 1 illustrates a chemical detection system for detecting at least one target chemical species, in accordance with one embodiment of the present invention. The chemical detection system 10 includes a self-sensed cantilevered probe array 20 with a plurality of self-sensed cantilevered probes 30. Self-sensed cantilevered probes have suspended cantilevered elements with a piezoelectric drive 32 comprised of a deposited layer of zinc oxide (ZnO), lead zircanate titinate (PZT), or other piezoelectric material that bends, deflects and vibrates the cantilevered element when excited or actuated with an applied drive voltage. The piezoelectric material generates a voltage as the cantilevered probes bend or vibrate, and can be used to sense cantilevered probe motions as well as drive cantilevered probes 30, referred to herein as self-sensing. At least one chemical-sensitive coating material 34 is applied to one or more cantilevered probes 30 in cantilevered probe array 20 to allow for chemical detection and specificity. One or more cantilevered probes 30 in cantilevered probe array 20 is coated or otherwise treated to detect target chemical species 12. An interface circuit 40, which is coupled to cantilevered probe array 20, actuates and senses motions of cantilevered probes 30. When cantilevered probe array 20 is exposed to a target chemical species 12 and is actuated by interface circuit 40, one or more cantilevered probes 30 in cantilevered probe array 20 exhibit a shifted cantilevered probe response.

Cantilevered probes 30 in cantilevered probe array 20 are frequency-differentiated such that cantilevered probes 30 having different masses or effective spring constants exhibit different resonant frequencies. Cantilevered probes 30 can be manufactured, for example, with small differences in cantilever lengths, resulting in separations in resonant frequencies so that the resonant frequency of each cantilevered probe 30 in an array is able to be detected with as few as two wires connected to cantilevered probe array 20. Thus, cantilevered probe arrays 20 with two or more cantilevered probes 30 can be packaged and connected to interface circuit 40 with a minimal number of bond pads, interconnection traces and bond wires to external interface and control electronics. Parallel arrays of cantilevered probes 30 can be configured with elements that number from a few to massively parallel arrays with a million or more cantilevered probes 30 on one substrate or die. Groups of cantilevered probe arrays 20 may be connected during on-chip trace definition, while wire-bonding to a leadframe or package, or at the socket or board level.

Non-overlapping, independent and orthogonal chemical-sensing effects on individual cantilevered probes 30 in cantilevered probe array 20 may be desirable but not necessary when many cantilevered probes 30 with various coatings and coating thicknesses are used for detection. Signal processing and pattern recognition of the resonance-frequency data from multiple cantilever probes 30 may be employed to differentiate between various target chemical species in varying concentrations having sometimes small and sometimes null effects. Differentiation between similar chemical substances can be made and their constituency and concentration can be determined in a system where a variety of coatings are applied to multiple cantilevered probes 30. Chemical detection system 10 can detect one or more target chemical species 12 such as mercury, hydrogen, an alcohol, water vapor, an explosive material, a chemical element, a chemical compound, an organic material, an inorganic material, a gaseous substance, a liquid, a biological material, a DNA strand, a bioactive agent, a toxin, and a combination thereof. Chemical species refers to any chemical or biological material.

One or more cantilevered probes 30 respond when exposed to target chemical species 12. Cantilevered probes 30 may respond by absorbing, adsorbing, or otherwise reacting to target chemical species 12. When exposed to target chemical species 12, cantilevered probes 30 may increase or decrease in mass, or become more rigid or less rigid. In one example, cantilevered probe 30 comprises a patterned layer of gold. When exposed to mercury, the two react to form an amalgam. The gold-mercury amalgam adds mass to cantilevered probe 30 and therefore tends to decrease the resonant frequency of cantilevered probe 30. Amalgam formation, however, increases the mechanical stiffness of cantilevered probe 30 thereby increasing its natural resonant frequency. The two effects tend to cancel each other, though one effect can be made dominant by careful selection and placement of chemical-sensitive coating material 34 on cantilevered probe 30.

Target chemical species 12, which may be located in a liquid or gas carrier 14 such as air or water, in a low-pressure gas, or a plasma, are transported in a forced or free manner towards cantilevered probes 30 where they contact surfaces of cantilevered probes 30 and invoke shifts in resonant frequency, Q factor, impedance, or deflection amplitudes.

Cantilevered probe array 20 is actuated with an excitation voltage applied to piezoelectric drive 32 disposed on each cantilevered probe 30 in cantilevered probe array 20. To reduce the number of external connections, a group of cantilevered probes 30 may be connected in series and electrically connected to a pair of cantilevered probe array drive pads 24, which in turn is electrically connected to interface circuit 40. While this configuration can increase the series resistance of the string, differentiation of individual cantilevered probes 30 may be made with detection of signals at or near the resonant frequency of selected cantilevered probe 30. Alternatively, a group of cantilevered probes 30 may be connected in parallel and electrically connected to a pair of cantilevered probe array drive pads 24, increasing the effective capacitance and decreasing the effective resistance, while still allowing differentiation of individual cantilevered probe responses based on frequency. Alternatively, cantilevered probes 30 may be connected in a network of series-connected and parallel-connected cantilevered probes with frequency-identifiable addressable elements.

Interface circuit 40 provides excitation voltages for the piezoelectric material on cantilevered probes 30 and senses deflections and vibrations of cantilevered probes 30 with the same piezoelectric material. In one example, interface circuit 40 includes an adjustable frequency generator that is scanned through a predetermined frequency range to excite one or more cantilevered probes 30 in cantilevered probe array 20. In another example, interface circuit 40 includes an impedance analyzer that is scanned through a resonant frequency of at least one cantilevered probe 30, measuring the magnitude and phase from cantilevered probes 30 and monitoring for any variations in the impedance as cantilevered probes 30 are exposed to one or more target chemical species 12. In another example, interface circuit 40 includes an oscillator circuit operating at a resonant frequency of at least one cantilevered probe 30 in cantilevered probe array 20. In another example, interface circuit 40 includes an oscillator circuit operating at a predetermined frequency that is near, yet off-resonance with respect to one or more cantilevered probes 30 in cantilevered probe array 20, so that as the resonant frequency of the selected cantilevered probe 30 shifts, a large output signal can be obtained as the resonant frequency shifts and moves towards the predetermined frequency, resulting in higher amplitudes of vibration and therefore higher output signals. The predetermined frequency may be set, for example, slightly above or slightly below the resonant frequency of one of cantilevered probes 30. In another example, the amplitude of bending and vibration is monitored as cantilevered probe 30 strikes against a fixed or adjustable mechanical stop such as a piezoelectric slab or a piezotube. In another example, interface circuit 40 includes an impulse circuit for applying an electrical impulse to cantilevered probe array 20, and ring-down of cantilever probes 30 is monitored. In another example, noise such as pink noise or white noise is applied to excite cantilevered probe array 20. In another example, interface circuit 40 includes a network analyzer for detecting signals from cantilevered probe array 20. Interface circuit 40 or controller 50 may include a fast Fourier transform generator to perform a fast Fourier transform (FFT) on the shifted cantilevered probe response and provide respective frequencies of cantilevered probes 30 in cantilevered probe array 20 for correlation with previously measured probe responses and determination of target chemical species 12.

Interface circuit 40 detects shifted cantilevered probe responses from one or more actuated cantilevered probes 30 in cantilevered probe array 20. Shifted cantilevered probe responses include, for example, a shift in a resonant frequency of one or more cantileveted probes 30, a shift in a quality (Q) factor of one or more cantilevered probes 30, a shift in impedance of one or more cantilevered probes 30, a shift in deflection amplitude of one or more cantilevered probes 30, or a combination thereof. With exposure to target chemical species 12, one or more cantilevered probes 30 in cantilevered probe array 20 can exhibit shifts. Similarly, with exposure to more than one target chemical species 12, one or more cantilevered probes 30 in cantilevered probe array 20 may exhibit shifts from which multiple target chemical species 12 can be determined.

A controller 50 such as a central processing unit (CPU), a digital signal processor (DSP), a microcontroller, or a field-programmable gate array (FPGA) may be included in chemical detection system 10 to execute programmed code and provide monitoring, controlling and analyzing functions. Controller 50 is in electrical communication with interface circuit 40 and may be located, for example, on substrate 22 along with cantilevered probe array 20, within enclosure 60 on the same circuit board or in the same package as cantilevered probe array 20, or located remotely with respect to enclosure 60. Controller 50 may internally contain the functions and capabilities of interface circuit 40. Controller 50 receives shifted cantilevered probe responses from a set of one or more cantilevered probes 30 in cantilevered probe array 20. Target chemical species 12 may be determined based on the shifted cantilevered probe response using, for example, an algebraic model that relates shifts in cantilevered probe responses to target chemical species and concentration. Alternatively, target chemical species 12 may be determined based on a comparison between the shifted cantilevered probe responses and a reference set of cantilevered probe responses. Such reference sets can be obtained by exposing cantilevered probes 30 to controlled environments with known target chemical species and concentrations during calibration at the factory or on site. Controller 50 can determine one or more target chemical species 12 through pattern recognition techniques, statistical processes, and fuzzy logic with comparison to the reference set of cantilevered probe responses. The reference set of cantilevered probe response comprises, for example, a learned set obtained from shifts in cantilevered probe responses by cantilevered probes 30 that are exposed to known target chemical species and concentrations under controlled laboratory or factory environments.

Chemical-sensitive coating material 34 is applied to at least a portion of one or more cantilevered probes 30 of cantilevered probe array 20. For example, chemical-sensitive coating material 34 may be applied to the topside or bottom side of one or more cantilevered probes 30 or to portions thereof. Chemical-sensitive coating material 34 includes, for example, an epoxy resin such as Novolac™, a fluoropolymer such as FluoroPel™, a gold layer, a palladium layer, an alcohol-absorbent polymer, a water-absorbent material, a chemical-sensitive polymer, a chemical-sensitive layer, a biosensitive material, a thiol, and combinations thereof.

Various application methods are used to deposit or apply coating materials and to treat surfaces of cantilevered probes 30. Chemical-sensitive coating materials 34 comprise, for example, a dipped coating, a sprayed coating, or a dispensed coating disposed on at least of portion of one or more cantilevered probes 30. An exemplary chemical-sensitive coating material 34 includes a masked coating disposed on a portion of one or more cantilevered probes 30. In an alternative application method, a non-homogeneous coating material is applied to a set of cantilevered probes 30 in cantilevered probe array 20, such that constituents of the non-homogeneous coating material are deposited on cantilevered probes 30 with suitable variations in composition, coverage, and thickness.

In one embodiment of the present invention, chemical detection system 10 includes one or more reference cantilevered probes in the cantilevered probe array. The reference cantilevered probe provides a reference cantilevered probe response when cantilevered probe array 20 is exposed to target chemical species 12. Reference cantilevered probes are formed, for example, with no coating materials disposed thereon to reduce or eliminate sensitivity to target chemical species 12. Alternatively, reference cantilevered probes have an inert coating disposed on the surface to reduce or eliminate sensitivity to target chemical species 12. Alternatively, one or more reference cantilevered probes are mechanically isolated from exposure to target chemical species 12 while other portions of cantilevered probe array 20 are exposed.

In cases where heating of select cantilevered probes 30 burns off, evaporates off, or otherwise cleans and resets cantilevered probe 30 to a nascent condition, a resistive heater 36 may be coupled to at least one cantilevered probe 30 in the cantilevered probe array 20. Resistive heater 36 may be formed with a resistive layer disposed on the surface of or formed within cantilevered probe 30. Exemplary resistive heaters 36, which may be connected in series or parallel or individually connected are formed on one, several, or all cantilevered probes 30 within cantilevered probe array 20. Resistive heaters 36 also may be used to react a target chemical species on cantilevered probe 30 by heating the probe to a predetermined temperature where the reaction can occur. Alternatively, resistive heaters 36 may be used to ignite or deflagrate condensate of explosive vapors on cantilevered probes 30.

Species attraction electrodes 38 disposed on cantilevered probes 30 can be used to apply voltage to preferentially attract target chemical species 12 or to allow the monitoring of electrochemical reactions in the vicinity of cantilevered probes 30. Species attraction electrodes 38, which may be disposed on one or more cantilevered probes 30 in cantilevered probe array 20, allow the application of a species attraction potential.

Exemplary chemical detection system 10 contains one or more cantilevered probe arrays 20 in an enclosure 60, which includes an inlet port 62 and an outlet port 64 for transport of target chemical species 12 and carriers 14. Target chemical species 12 enters enclosure 60 through inlet port 62 and is exposed to cantilevered probe array 20. Target chemical species 12 or by-products thereof exit through outlet port 64. Enclosure 60 may include filters, scrubbers, and other media treatment elements to aid in the detection of target chemical species 12.

A transport mechanism 66 such as a pump or a fan with ductwork or piping may be included for transporting target chemical species 12 to cantilevered probe array 20.

A concentrator 68 such as a pressurizing system or a condenser and heater system may be included to concentrate target chemical species 12 proximal to cantilevered probe array 20 for detection of target chemical species 12.

Chemical detection system 10 may be connected to a local area network (LAN), a wide area network (WAN), the Internet, or other networked communication system via one or more wired or wireless connections.

Chemical detection system 10 may be installed, for example, into an air handling system of a building or airport that has many inlets, into a standalone unit with a portal for chemical detection, and into handheld units for portable use. Chemical detection system 10 may be installed in shipping containers and crates during storage and transit for chemical detection and monitoring.

Figure 2:
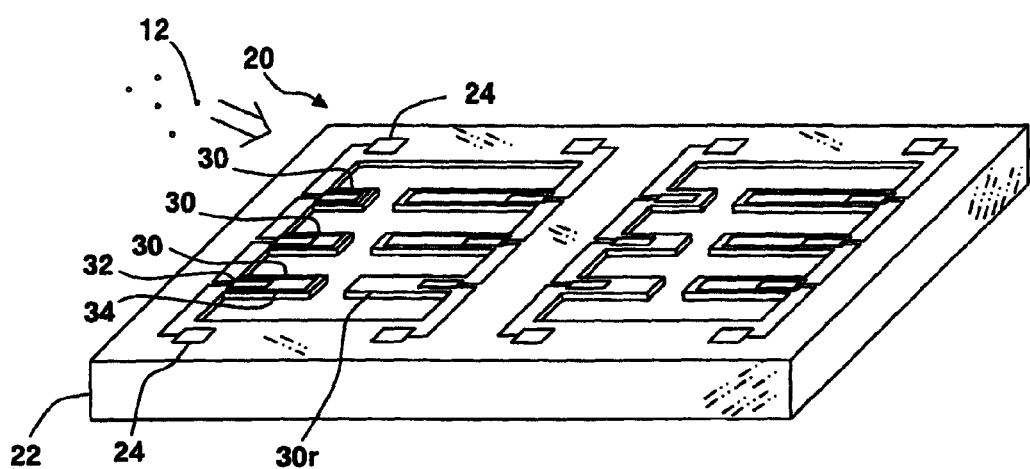
FIG. 2 illustrates a self-sensed cantilevered probe array, in accordance with one embodiment of the current invention.

FIG. 2 illustrates a self-sensed cantilevered probe array, in accordance with one embodiment of the present invention. Self-sensed cantilevered probe array 20 includes a plurality of cantilevered probes 30 on a substrate 22. At least one chemical-sensitive coating material 34 is applied to one or more cantilevered probes 30 in cantilevered probe array 20. Variations in length or thickness of cantilevered probes 30 and variations in the thickness and coverage of applied coatings allow frequency differentiation between cantilevered probes within cantilevered probe array 20.

Cantilevered probes 30 may have a rectangular shape, though other shapes may be suitably used such as a pointed cantilever, a V-shaped cantilever, a triangular-shaped cantilever, a dual-arm cantilever, or a balanced cantilever. Cantilevered probes 30 may be arranged and attached to substrate 22 in an array of cantilevered beams, the cantilevers being all identical, all different, or some combination thereof.

Cantilevered probe array 20 is actuated with an excitation voltage applied to a piezoelectric drive 32 of piezoelectric material disposed on each cantilevered probe 30. Cantilevered probes 30 may be series-connected to a pair of cantilevered probe array drive pads 24 on substrate 22. Alternatively, cantilevered probes 30 may be parallel-connected to the pair of cantilevered probe array drive pads 24. Alternatively, cantilevered probe array 20 may comprise a network of series-connected and parallel-connected cantilevered probes electrically connected to the pair of cantilevered probe array drive pads 24. More than one group or array of cantilevered probes 30 may be included on substrate 22. Substrate 22 may have through-wafer vias for backside connection.

Substrate 22 includes a semiconductor substrate such as a silicon wafer, a silicon-on-insulator (SOI) wafer, a glass substrate, or other suitable substrate for forming cantilevered probes 30 thereon. Cantilevered probes 30 comprise materials such as silicon, polysilicon, silicon nitride, a metal film, a metal sheet, a zinc oxide film, a PZT film, a polymeric layer, and combinations thereof. For example, a zinc oxide film is deposited on a layer of single-crystal silicon, patterned, and etched. Conductive layers for top and bottom electrodes, interconnections, and heater connections are deposited and etched accordingly. Definition of cantilevered probes 30 with a photomask and associated lithographic sequences along with deep reactive ion etching (D-RIE) or anisotropic etching of the cantilevers and substrate allows the formation and freeing of silicon cantilevers with interconnected ZnO electrodes in series, parallel, and series-parallel configurations. Excitation and detection of the cantilevers occur with voltages applied to the piezoelectric material and detection thereof.

Chemical-sensitive coating material 34 is applied to at least a portion of one or more cantilevered probes 30. The chemical-sensitive coating material includes, for example, an epoxy resin, a fluoropolymer, a gold layer, a palladium layer, an alcohol-absorbent polymer, a water-absorbent material, a chemical-sensitive polymer, a chemical-sensitive layer, a biosensitive material, a thiol, and a combination thereof. Chemical-sensitive coating material 34 may be applied, for example, with techniques such as dipping, spraying, or dispensing the coating on at least a portion of one or more cantilevered probes. The chemical-sensitive coating material may be applied onto a portion of one or more cantilevered probes with the use of stencil masks or photomasks and photolithographic patterning techniques. Chemical-sensitive coating material 34 may be applied, for example, using standard sputtering and other deposition techniques known in the art.

Multiple masking sequences can be used to apply multiple coating materials. Alternatively, multiple-component chemical-sensitive coating materials 34 may comprise a non-homogeneous coating material applied to a set of cantilevered probes 30 in the cantilevered probe array 20, applied in such a way that variations in coating thickness and composition occur when they are deposited.

When exposed to target chemical species 12, one or more cantilevered probes 30 in cantilevered probe array 20 may undergo an electrical or a mechanical shift, such as a shifted resonant frequency, a shifted Q factor, a shifted impedance, or a shifted deflection amplitude.

Cantilevered probe array 20 may include one or more reference cantilevered probes 30r to provide a reference cantilevered probe response when cantilevered probe array 20 is exposed to target chemical species 12. For example, reference cantilevered probes may be uncoated, coated with an inert material, or otherwise protected from exposure to target chemical species 12.

Figure 3:
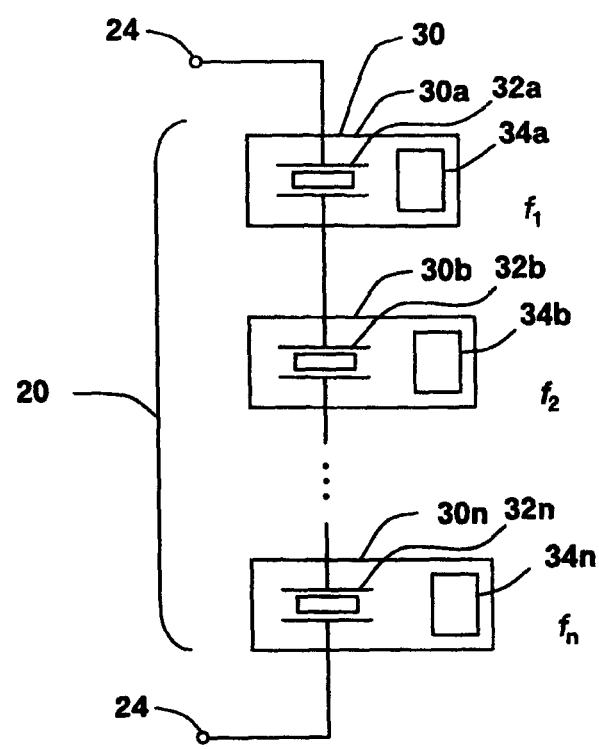
FIG. 3 is a schematic diagram of a cantilevered probe array with series-connected cantilevered probes electrically connected to a pair of cantilevered probe array drive pads, in accordance with one embodiment of the current invention.

FIG. 3 is a schematic diagram of a cantilevered probe array with series-connected cantilevered probes electrically connected to a pair of cantilevered probe array drive pads, in accordance with one embodiment of the present invention. Two or more cantilevered probes 30 in a cantilevered probe array 20 are connected in series to a pair of cantilevered probe array drive pads 24. Electrodes above and below the piezoelectric material on each cantilevered probe 30 are connected in series with electrodes above and below the piezoelectric material on other cantilevered probes 30 in the set. In the example illustrated, cantilevered probes 30a, 30b, . . . 30n represent a plurality of series-connected cantilevered probes with piezoelectric drives 32a, 32b, . . . 32n that are frequency-differentiated with fundamental resonant frequencies f1, f2, . . . fn, respectively. Each cantilevered probe 30a, 30b, . . . 30n may have one or more chemical-sensitive coating materials 34a, 34b, . . . 34n coated thereon. When activated, for example, with an interface circuit (not shown) that scans through the resonant frequencies of one or more cantilevered probes, each cantilevered probe within the scanned frequency range is, in turn, excited and oscillated by the interface circuit as the frequency of the oscillator or frequency generator is scanned through its resonant frequency. Multiple groups of series-connected cantilevered probes 30 may be further connected in series or in parallel to cantilevered probe array drive pads 24 or to other sets of drive pads.

Figure 4:
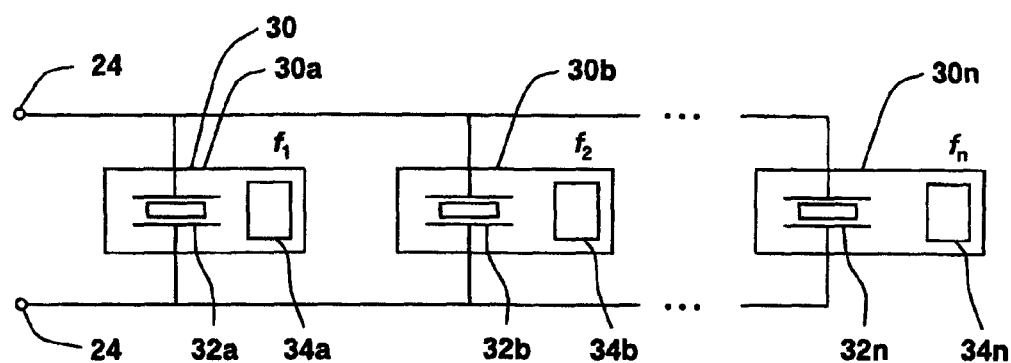
FIG. 4 is a schematic diagram of a cantilevered probe array with parallel-connected cantilevered probes electrically connected to a pair of cantilevered probe array drive pads, in accordance with one embodiment of the current invention.

FIG. 4 is a schematic diagram of a cantilevered probe array with parallel-connected cantilevered probes electrically connected to a pair of cantilevered probe array drive pads, in accordance with one embodiment of the present invention. Two or more cantilevered probes 30 are connected in parallel to a pair of cantilevered probe array drive pads 24. Electrodes above and below the piezoelectric material on each cantilevered probe 30 are connected in parallel with electrodes above and below the piezoelectric material on other cantilevered probes 30 in the set. In the example illustrated, cantilevered probes 30a, 30b, . . . 30n represent a plurality of parallel-connected cantilevered probes with piezoelectric drives 32a, 32b, . . . 32n that are frequency-differentiated with fundamental resonant frequencies f1, f2, . . . fn, respectively. Each cantilevered probe 30a, 30b, . . . 30n may have one or more chemical-sensitive coating materials 34a, 34b, . . . 34n coated thereon. When activated, for example, with an interface circuit (not shown) that scans through the resonant frequencies of one or more cantilevered probes, each cantilevered probe is, in turn, excited and oscillated by the interface circuit as the frequency of the oscillator or frequency generator is scanned through the resonant frequency. Multiple groups of parallel-connected cantilevered probes 30 may be further connected in series or in parallel to cantilevered probe array drive pads 24 or to other sets of drive pads.

Figure 5:
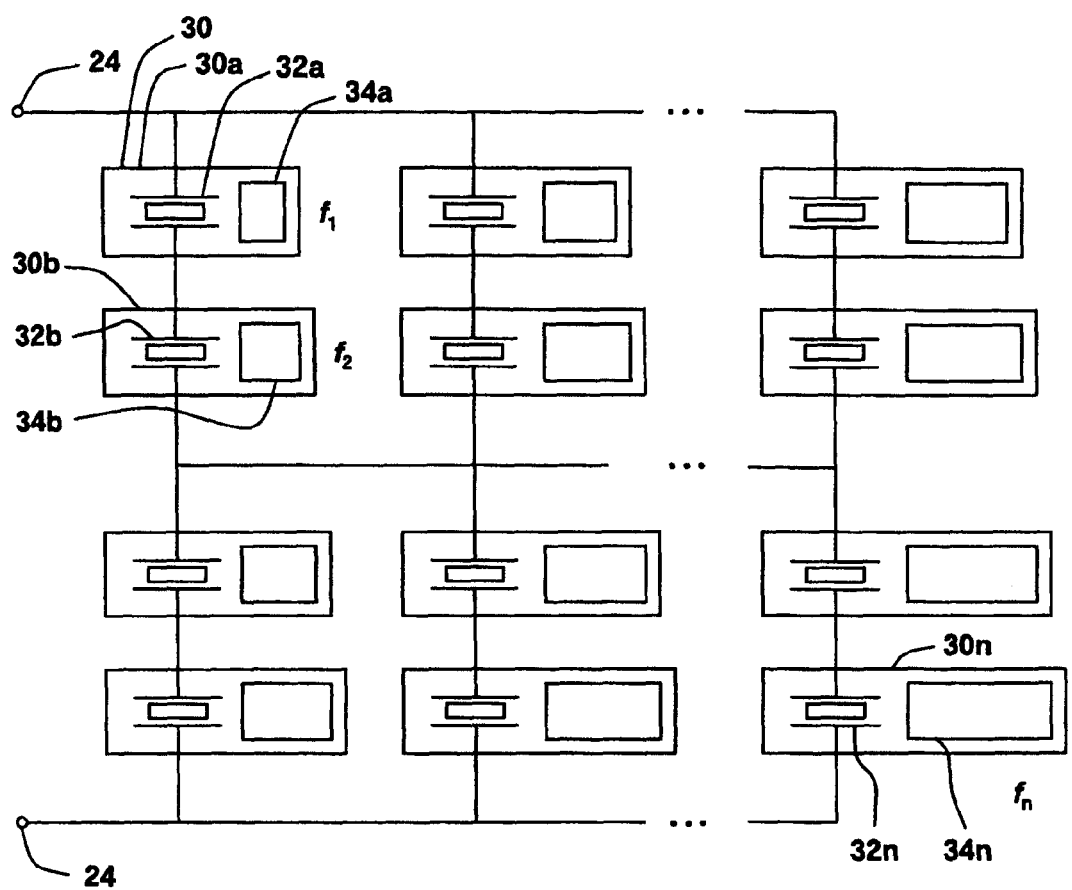
FIG. 5 is a schematic diagram of a cantilevered probe array with a network of series-connected and parallel-connected cantilevered probes electrically connected to a pair of cantilevered probe array drive pads, in accordance with one embodiment of the current invention.

FIG. 5 is a schematic diagram of a cantilevered probe array with a network of series-connected and parallel-connected cantilevered probes electrically connected to a pair of cantilevered probe array drive pads, in accordance with one embodiment of the present invention. A plurality of cantilevered probes 30 is connected in a network of series and/or parallel sets of cantilevered probes 30 to a pair of cantilevered probe array drive pads 24. In the example illustrated, cantilevered probes 30a, 30b, . . . 30n represent series-connected and parallel-connected cantilevered probes with piezoelectric drives 32a, 32b, . . . 32n that are frequency-differentiated with fundamental resonant frequencies f2, . . . fn. Each cantilevered probe 30a, 30b, . . . 30n may have one or more chemical-sensitive coating materials 34a, 34b, . . . 34n coated thereon. When activated, for example, with an interface circuit (not shown) that scans through the resonant frequencies of one or more cantilevered probes 30, each cantilevered probe 30 is, in turn, excited and oscillated by the interface circuit as the frequency of the oscillator or frequency generator is scanned through the resonant frequency. Multiple groups of networked cantilevered probe arrays 20 may be located on the same substrate and connected to other pairs of drive pads.

Figure 6A:
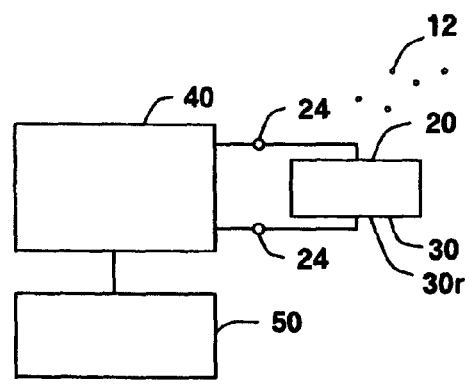
FIG. 6a is a schematic diagram of a controller and an interface circuit connected to a self-sensed cantilevered probe array, in accordance with one embodiment of the current invention.

FIG. 6a is a schematic diagram of a controller and an interface circuit connected to a self-sensed cantilevered probe array, in accordance with one embodiment of the present invention. Controller 50 is connected to interface circuit 40 that drives and senses a plurality of self-sensed cantilevered probes 30 in a cantilevered probe array 20. It should be observed that cantilevered probe array 20 may be electrically connected to interface circuit 40 with as few as two cantilevered probe array drive pads 24. At least one cantilevered probe 30 in cantilevered probe array 20 exhibits a shifted cantilevered probe response when cantilevered probe array 20 is exposed to target chemical species 12 and cantilevered probe array 20 is actuated by interface circuit 40.

Interface circuit 40 actuates cantilevered probe array 20 with an excitation voltage applied to a piezoelectric material disposed on each cantilevered probe 30 in the cantilevered probe array 20. In one example, interface circuit 40 includes an adjustable frequency generator that is scanned through a predetermined frequency range. In another example, interface circuit 40 includes an impedance analyzer that is scanned through a resonant frequency of one or more cantilevered probes 30 in cantilevered probe array 20. In another example, interface circuit 40 includes an oscillator circuit operating at a resonant frequency of at least one cantilevered probe in the cantilevered probe array. In another example, interface circuit 40 includes an oscillator circuit operating at a predetermined frequency that is set to be off-resonance with respect to at least one cantilevered probe 30 in cantilevered probe array 20. In another example, interface circuit 40 includes control circuitry to monitor the amplitude of bending and vibration as cantilevered probe 30 strikes against a fixed or adjustable mechanical stop. In another example, interface circuit 40 comprises an impulse circuit for applying an electrical impulse to all cantilevered probes 30 in cantilevered probe array 20. In another example, interface circuit 40 or controller 50 includes a fast Fourier transform generator to perform a fast Fourier transform on the shifted cantilevered probe response. Interface circuit 40 detects a shifted cantilevered probe response from one or more actuated cantilevered probes 30 such as a shifted resonant frequency, a shifted Q factor, a shifted impedance, or a shifted deflection amplitude.

Controller 50 receives a shifted cantilevered probe response from a set of one or more cantilevered probes 30 in cantilevered probe array 20. The target chemical species is determined based on the shifted cantilevered probe response. For example, the target chemical species may be determined based on a comparison between the shifted cantilevered probe response and a reference set of cantilevered probe responses. The reference set of cantilevered probe responses comprises, for example, a learned set obtained during the calibration of the chemical-sensing system or from a statistical database of cantilevered probe responses.

To cancel out common mode effects such as temperature, one of the cantilevered probes 30 in the cantilevered probe array 20 may be a reference cantilevered probe 30r, wherein the reference cantilevered probe 30r provides a reference cantilevered probe response when cantilevered probe array is exposed to target chemical species 12.

Figure 6B:
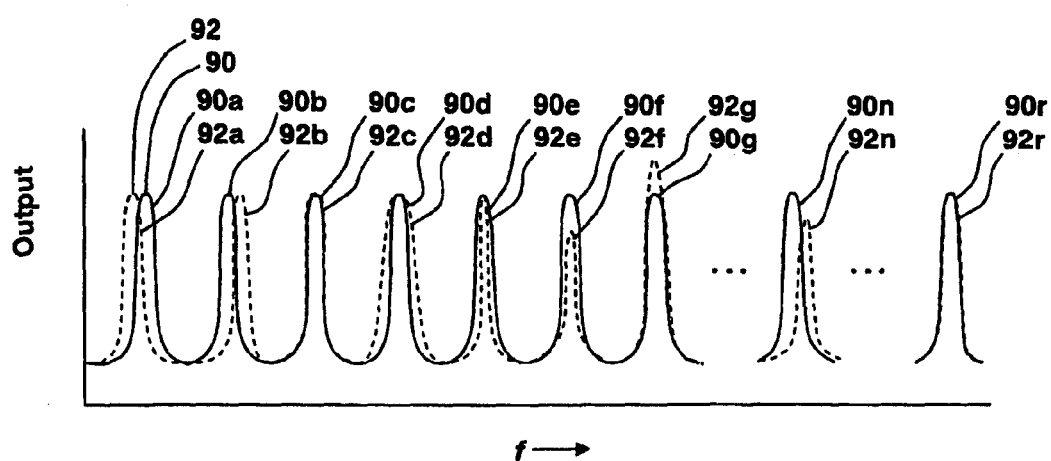
FIG. 6b is a plot of cantilevered probe responses from a self-sensed cantilevered probe array scanned through a predetermined frequency range, in accordance with one embodiment of the current invention.

FIG. 6b shows an illustrative plot of cantilevered probe responses from a self-sensed cantilevered probe array scanned through a predetermined frequency range, in accordance with one embodiment of the present invention. When activated, for example, with an interface circuit that scans through the resonant frequencies of one or more cantilevered probes, each cantilevered probe is, in turn, excited and oscillated by the interface circuit as the frequency of the oscillator or frequency generator is scanned through the resonant frequency. Depending on the type and amount of a target chemical species and the coating on the cantilevered probe, the cantilevered probes in the array may exhibit shifted cantilevered probe responses such as a shifted resonant frequency, a shifted Q factor, a shifted impedance, a shifted deflection amplitude, or a combination thereof.

Output curve 90 shows exemplary output signals from an array of cantilevered probes excited through a frequency range that includes a resonant frequency of each of the cantilevered probes in the array. Output curve 90 shows a baseline or reference set of resonant peaks 90a, 90b, 90c, 90d, 90e, 90f, 90g and 90n corresponding to a set of eight frequency-differentiated cantilevered probes with nominally equal frequency separations between the cantilevered probes. When the cantilevered probe array is exposed to a target chemical species and is actuated by the interface circuit, at least one cantilevered probe in the cantilevered probe array exhibits a shifted cantilevered probe response.

Exemplary output curve 92 shows resonant peaks 92a, 92b, 92c, 92d, 92e, 92f, 92g and 92n corresponding to the set of eight frequency-differentiated cantilevered probes after exposure to one or more target chemical species. In the example illustrated, resonant peak 92a of the first cantilevered probe is shifted downwards from resonant peak 90a after chemical exposure. Resonant peak 92b of the second cantilevered probe is shifted higher than resonant peak 90b. Resonant peak 92c of the third cantilevered probe remains the same as resonant peak 90c. Resonant peak 92d of the fourth cantilevered probe has a lower Q factor than resonant peak 90d after chemical exposure. Resonant peak 92e of the fifth cantilevered probe has a higher Q factor than resonant peak 90e after chemical exposure. Resonant peak 92l has an amplitude less than that of resonant peak 90f after chemical exposure, and resonant peak 92g has an amplitude greater than that of resonant peak 90g after chemical exposure. Resonant peak 92n exhibits a combination of shifts in frequency, Q factor and amplitude after chemical exposure.

An additional resonant peak 92r corresponding to a reference cantilevered probe shows no change in cantilevered probe response after exposure to the target chemical species compared to resonant peak 90r corresponding to the reference cantilevered probe prior to exposure.

Figure 7:
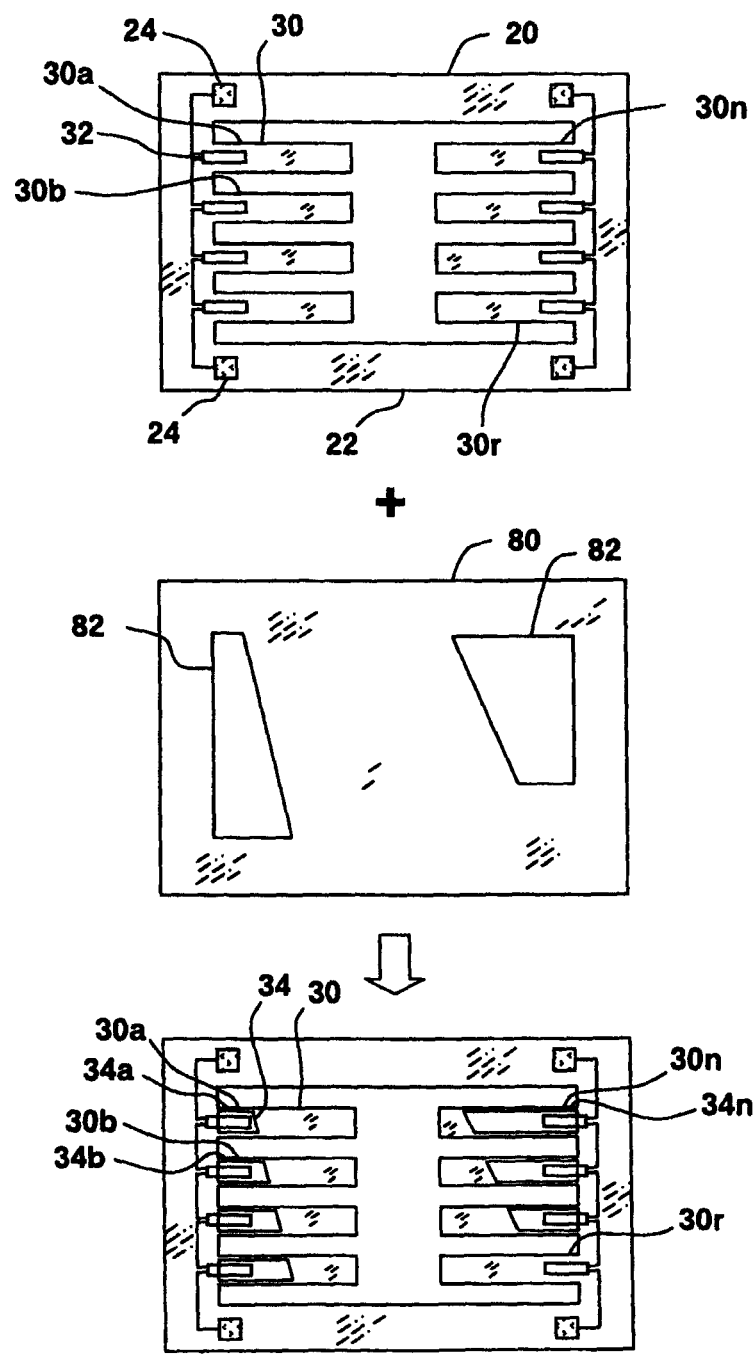
FIG. 7 illustrates a method for applying a chemical-sensitive coating material to a cantilevered probe array with a mask, in accordance with one embodiment of the current invention.

FIG. 7 illustrates a chemical-sensitive coating material applied to a cantilevered probe array with a mask, in accordance with one embodiment of the present invention. A stencil mask 80 including at least one aperture 82 is positioned on or above a surface of a self-sensed cantilevered probe array 20 having a plurality of self-sensed cantilevered probes 30. A chemical-sensitive coating material 34 is selectively applied to cantilevered probe array 20 through apertures 82. In the example shown, cantilevered probes 30a, 30b, ... 30n are selectively coated with chemical-sensitive coating material 34 by spraying the material through stencil mask 80 and then drying chemical-sensitive coating material 34a, 34b, ... 34n on cantilevered probes 30a, 30b, ... 30n, respectively. A reference cantilevered probe 30r is shown with no coating, having been masked with stencil mask 80 during spraying.

In this example, cantilevered probes 30a, 30b, ... 30n are nominally the same size and thickness. Frequency differentiation for this set of cantilevered probes is achieved by varying the area of the cantilevered probes that is covered by the coating. An angled aperture 82 in stencil mask 80 allows different amounts of coating material to be disposed on each cantilevered probe, varying the mass on each cantilevered probe and thereby changing the resonant frequencies accordingly. Stencil mask 80 may be used to cover cantilevered probe array drive pads 24 and other portions of substrate 22 that need not be coated. Piezoelectric drives 32 on cantilevered probes 30a, 30b, ... 30n and 30r, respectively, may be coated, partially coated, or uncoated with chemical-sensitive coating materials 34.

Figure 8:
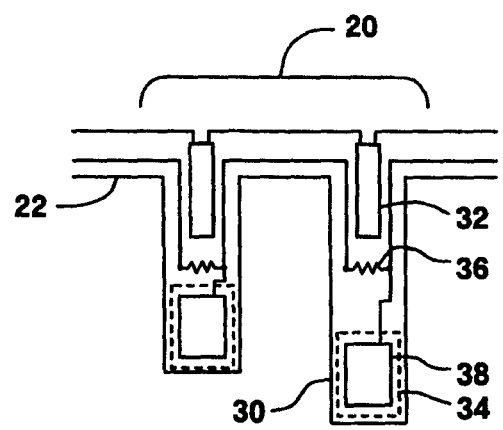
FIG. 8 illustrates a top view of a self-sensed cantilevered probe including a selectively deposited coating, a heater, and a species attraction electrode.

FIG. 8 illustrates a top view of a self-sensed cantilevered probe including a selectively deposited coating, a heater, and a species attraction electrode. A resistive heater 36 is disposed on or formed in cantilevered probe 30. Resistive heater 36 allows cantilevered probe 30 to be heated, for example, to initialize cantilevered probe 30 prior to exposing cantilevered probe array 20 to the target chemical species. In another role, resistive heater 36 may be used to burn off, deflagrate, or otherwise react a target chemical species that deposits on a surface of cantilevered probe 30.

In another embodiment, a species attraction electrode 38 may be disposed on cantilevered probe 30 of cantilevered probe array 20 to allow a species attraction potential to be applied. Species attraction electrode 38 is positioned, for example, underneath or adjacent to chemical-sensitive coating material 34. Electrical connections to species attraction electrode 38 may be made with, for example, one end of piezoelectric drive 32, one end of resistive heater 36, or with a connection to an independent electrical trace on substrate 22.

Figure 9:
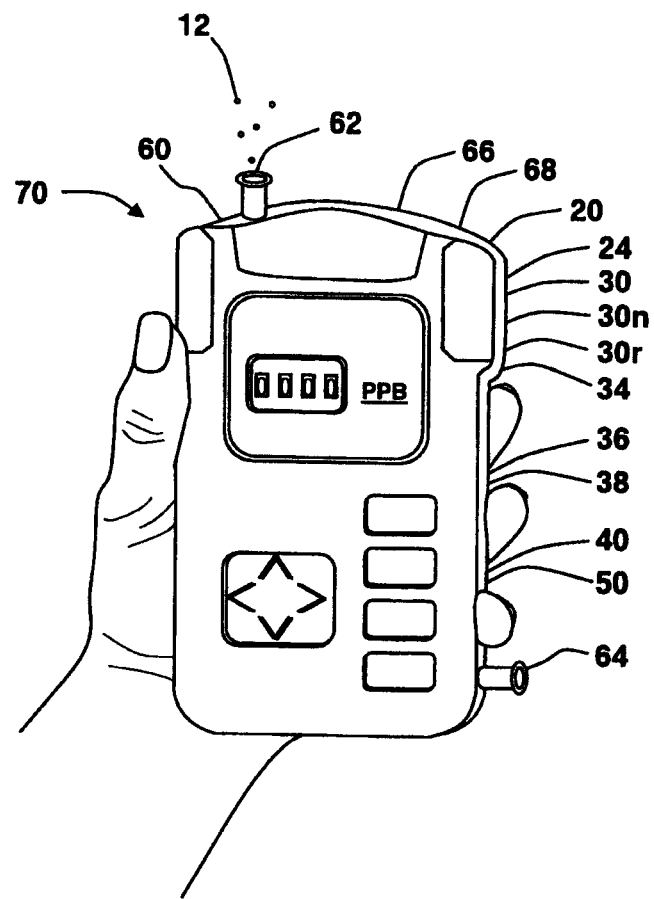
FIG. 9 illustrates a handheld system for sensing a target chemical species, in accordance with one embodiment of the current invention.

FIG. 9 illustrates a handheld system for sensing a target chemical species, in accordance with one embodiment of the present invention. Handheld system 70 includes an enclosure 60, a self-sensed cantilevered probe array 20, at least one chemical-sensitive coating material 34 applied to at least one self-sensed cantilevered probe 30 in cantilevered probe array 20, and an interface circuit 40 coupled to cantilevered probe array 20. Enclosure 60 has an inlet port 62 to allow ingression of target chemical species 12 into enclosure 60 and an outlet port 64 to allow egression of target chemical species 12 or a by-product thereof from enclosure 60. When cantilevered probe array 20 is exposed to target chemical species 12 and cantilevered probe array 20 is actuated by interface circuit 40, one or more cantilevered probes 30 in cantilevered probe array 20 exhibit a shifted cantilevered probe response.

Cantilevered probe array 20 includes a plurality of cantilevered probes 30 that are frequency-differentiated. The plurality of cantilevered probes 30 in cantilevered probe array 20 is electrically connected to a pair of cantilevered probe array drive pads, and one or more groups of cantilevered probes 30 may be included within enclosure 60.

Handheld system 70 may include a controller 50 in communication with interface circuit 40. Controller 50 receives a shifted cantilevered probe response from a set of cantilevered probes 30 in cantilevered probe array 20. The shifted cantilevered probe responses are analyzed and the constituency and concentration of target chemical species 12 may be determined based on the shifted cantilevered probe response.

Cantilevered probe array 20 may include a reference cantilevered probe 30r. The reference cantilevered probe 30r provides a reference cantilevered probe response when cantilevered probe array 20 is exposed to target chemical species 12.

One or more cantilevered probes 30 in cantilevered probe array 20 may have resistive heaters 36 to locally heat selected cantilevered probes 30. A species attraction electrode 38 may be disposed on one or more cantilevered probes 30 in cantilevered probe array 20 to allow application of a species attraction potential.

Handheld system 70 may include a transport mechanism 66 such as a pump, fan or blower and ductwork or piping for transporting target chemical species 12 to cantilevered probe array 20. Handheld system 70 may include a concentrator 68 such as a compressor or a condenser to concentrate target chemical species 12 proximal to one or more cantilevered probes 30 in cantilevered probe array 20.

Command and data entry input devices such as buttons, keypads, or softkeys, allow the selection of the function and operation of handheld system 70. Results of measurements are displayed on an output device such as an LCD, or communicated to another analysis system through a wired communication port such as a universal serial bus (USB) port or through a wireless communication protocol.

Figure 10:
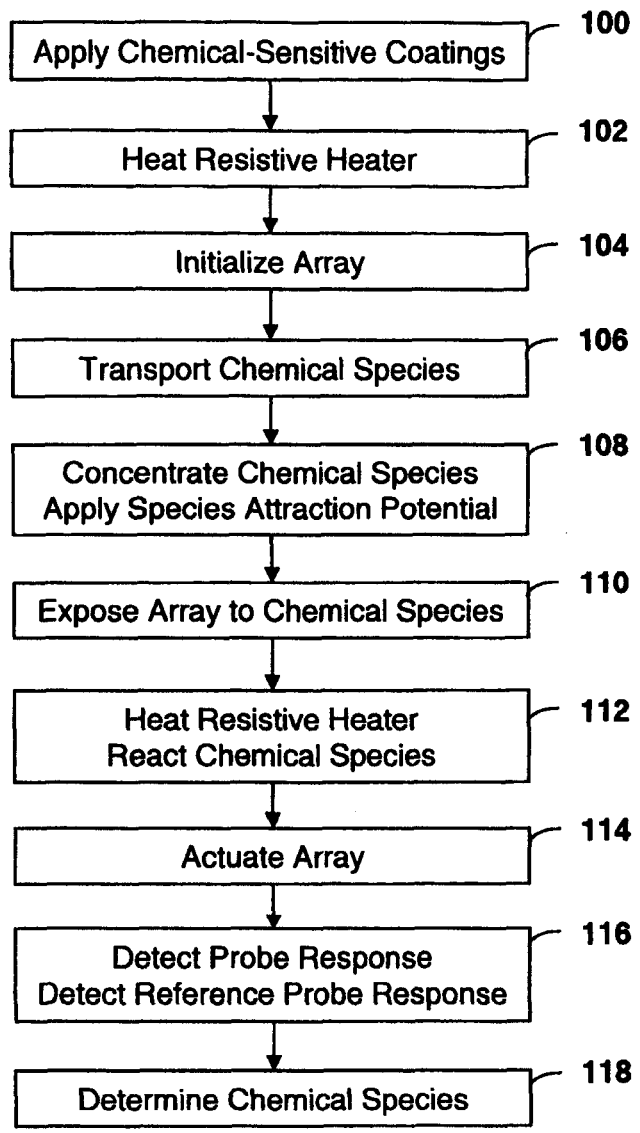
FIG. 10 is a flow chart of a method for chemical detection, in accordance with one embodiment of the current invention.

FIG. 10 is a flow chart of a method for chemical detection, in accordance with one embodiment of the present invention. The chemical detection method includes various steps to detect and identify one or more target chemical species with a self-sensed cantilevered probe array.

The cantilevered probes in the cantilevered probe array are frequency-differentiated, separated in the frequency domain such that any one of the cantilevered probes can be measured independently of the others using, for example, a frequency generator, a frequency synthesizer, a controlled oscillator, or an impedance analyzer when the cantilevered probes are configured in series or in parallel with other cantilevered probes. The cantilevered probe array includes, for example, at least two-series connected cantilevered probes electrically connected to a pair of cantilevered probe array drive pads. Alternatively, the cantilevered probe array includes at least two parallel connected cantilevered probes electrically connected to a pair of cantilevered probe array drive pads. Alternatively, the cantilevered probe array includes a network of series-connected and parallel-connected cantilevered probes electrically connected to a pair of cantilevered probe array drive pads. One or more groups of cantilevered probes may be connected to the same set of cantilevered probe array drive pads or to a different set of cantilevered probe array drive pads on the same substrate for external connection to an interface circuit.

After fabrication of the cantilevered probe array, a chemical-sensitive coating material may be applied to one or more cantilevered probes in the cantilevered probe array, as seen at block 100. The chemical-sensitive coating material may include, for example, an epoxy resin, a fluoropolymer, a gold layer, a palladium layer, an alcohol-absorbent polymer, a water-absorbent material, a chemical-sensitive polymer, a chemical-sensitive layer, a biosensitive material, a thiol, and combinations thereof.

The coating material may be applied, for example, by standard deposition techniques such as sputter depositions, electron beam depositions, or plasma-enhanced chemical vapor depositions, or by dipping, spraying or dispensing the coating material onto at least a portion of one or more cantilevered probes. The coating material may be applied, for example, with a stencil mask and selective masking of one or more cantilevered probes and applying the chemical-sensitive coating through the mask. A single material may be applied through the mask.

A plurality of chemical-sensitive coating materials may be applied to a set of cantilevered probes in the cantilevered probe array. For example, multiple masks may be used for multiple coatings with different coating materials on selected portions of one or more cantilevered probes. Alternatively, coating with multiple materials through a single mask may be accomplished by spraying a non-homogenous coating material onto a set of cantilevered probes in the cantilevered probe array such that cantilevered probes in the array are coated with substantive differences in coating constituency, thickness, or fraction of coverage.

When a resistive heater is used, the resistive heater that is coupled to at least one cantilevered probe is heated to initialize the cantilevered probe prior to exposing the cantilevered probe array to the target chemical species, as seen at block 102. The resistive heater locally heats up the cantilevered probe to an elevated temperature to evaporate, burn off, or otherwise remove residual materials from the surfaces of the cantilevered probe.

The array is initialized, as seen at block 104. Initialization of the array is accomplished, for example, by running a scan through the resonant frequencies of the cantilevered probes in the cantilevered probe array to establish a baseline or to ensure that all the cantilevered probes and the interface electronics are functioning properly.

The target chemical species may be transported to the cantilevered probe array, as seen at block 106. Fans, blowers, or pumps may be used, for example, to force flow of the target chemical species and a carrier gas or liquid onto the cantilevered probe array. Convective processes or normal diffusive processes due to concentration gradients may be used, for example, to transport the target chemical species to the cantilevered probe array for detection.

The target chemical species may be concentrated proximal to the cantilevered probe array, as seen at block 108. Concentration of the target chemical species may be accomplished, for example, with a compressor and a valve system to increase the pressure in the vicinity of the cantilevered probe array. A condenser and a heater may be used, for example, to collect samples of the target chemical species and then release it in proximity to the cantilevered probe array.

Selective attraction of chemical and biological species may be accomplished with, for example, a species attraction potential applied to a species attraction electrode disposed on at least one cantilevered probe in the cantilevered probe array.

The self-sensed cantilevered probe array is exposed to a target chemical species, as seen at block 110. The target chemical species may be in a liquid or a gas. A valve and associated piping may be used to expose the cantilevered probe array to the target chemical species and the carrier.

When embodied so, the resistive heater coupled to at least one cantilevered probe may be heated to react the target chemical species, as seen at block 112. Reaction of the target chemical species may be result, for example, in a volatile material that is desorbed from one or more cantilevered probes resulting in a shift in the resonant frequency due to less mass on the beam. Alternatively, reaction of the target chemical species may result in a formation of a material on the surface of the cantilevered probe that increases the vibrational stiffness of the cantilevered probe and produces a frequency shift. Alternatively, reaction of the target chemical species may result in a stressed film on the surface of the cantilevered probe that causes a static deflection of the cantilevered probe, which may be measured, for example, with a tapping mode where the cantilevered beam is tapped against a reference surface adjusted to be a fixed distance away from the cantilevered beam or with a tapping mode where the beam is tapped against an adjustable mechanical stop, adjusted to allow the cantilevered probe to tap a consistent amount against the mechanical stop.

The exposed cantilevered probe array is actuated, as seen at block 114. The exposed cantilevered probes are actuated, for example, by applying an excitation voltage to a piezoelectric material disposed on each cantilevered probe in the cantilevered probe array. In another example, the exposed cantilevered probe array is actuated with a frequency generator by scanning the cantilevered probes through a predetermined frequency range. In another example, the exposed cantilevered probe array is actuated by driving the exposed array at a resonant frequency of one cantilevered probe in the cantilevered probe array, then switching as desired to a resonant frequency of another cantilevered probe for additional measurements. In another example, the exposed cantilevered probe array is actuated by driving the exposed array at a predetermined frequency, wherein the predetermined frequency is off-resonance with respect to at least one cantilevered probe in the cantilevered probe array. In another example, the amplitude of vibration is controlled as the cantilevered probe strikes against a fixed or adjustable mechanical stop. In another example, the exposed cantilevered array is actuated with an electrical impulse applied to the cantilevered probe array.

A cantilevered probe response is detected from at least one self-sensed cantilevered probe in the cantilevered probe array, as seen at block 116. Detecting the cantilevered probe response from one or more actuated cantilevered probes comprises, for example, measuring a shifted resonant frequency, a shifted Q factor, a shifted impedance, a shifted deflection amplitude, and a combination thereof. A fast Fourier transform (FFT) may be performed on the cantilevered probe response from one or more actuated cantilevered probes. The entire array of cantilevered probes, a subset thereof, or an individual cantilevered probe may be addressed by selective actuation and detection.

With the availability of a reference cantilevered probe, a reference cantilevered probe response may be detected from one or more reference cantilevered probes in the cantilevered probe array.

The target chemical species is determined based on the detected cantilevered probe response, as seen at block 118. A controller or a software application running on a computer or digital device may be used to analyze the cantilevered probe responses and determine one or more components and their concentration in the sample. The target chemical species may be determined in part based on the detected reference cantilevered probe response, for example, by common mode correcting for effects such as temperature, pressure and viscosity of the sampled medium. The detected target chemical species may include, for example, mercury, hydrogen, an alcohol, water vapor, an explosive material, a chemical element, a chemical compound, an organic material, an inorganic material, a gaseous substance, a liquid, a biological material, a DNA strand, a bioactive agent, a toxin, and combinations thereof.

Using pattern recognition, modeling functions or signal processing techniques such as fuzzy logic, the target chemical species may be determined based on comparing a measured shift from one or more actuated cantilevered probes to a reference set of cantilevered probe response, and determining the target chemical species based on the reference set of cantilevered probe responses. The reference set of cantilevered probe responses may comprise, for example, a learned set from calibration runs or from a statistical database with expectation values for various target chemical species.

Figure 11:
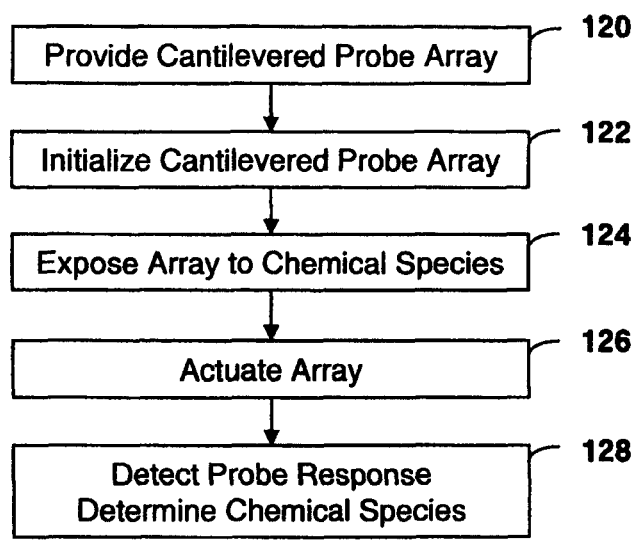
FIG. 11 is a flow chart of a method for chemical detection, in accordance with another embodiment of the current invention.

FIG. 11 is a flow chart of a method for chemical detection, in accordance with another embodiment of the present invention. The chemical detection method includes various steps to detect and identify one or more target chemical species with a self-sensed cantilevered probe array.

A self-sensed cantilevered probe array is provided, as seen at block 120. The cantilevered probes in the cantilevered probe array are frequency-differentiated, and may include at least two series-connected or parallel-connected cantilevered probes electrically connected to a pair of cantilevered probe array drive pads. Alternatively, the cantilevered probe array includes a network of series-connected and parallel-connected cantilevered probes electrically connected to a pair of cantilevered probe array drive pads.

The array is initialized, as seen at block 122. Initialization of the array is accomplished, for example, by running a scan through the resonant frequencies of the cantilevered probes in the cantilevered probe array to establish a baseline or to ensure that all the cantilevered probes and the interface electronics are functioning properly.

The self-sensed cantilevered probe array is exposed to a target chemical species, as seen at block 124. The target chemical species may be in a liquid or a gas. A valve and associated piping may be used to expose the cantilevered probe array to the target chemical species and the carrier.

The exposed cantilevered probe array is actuated, as seen at block 126. The exposed cantilevered probes are actuated, for example, by applying an excitation voltage to a piezoelectric material disposed on each cantilevered probe in the cantilevered probe array; by scanning the cantilevered probes through a predetermined frequency range; by driving the exposed array at a resonant frequency of at least one cantilevered probe in the cantilevered probe array; by driving the exposed array at a predetermined off-resonance frequency; by driving and controlling the tapping of the cantilevered probes against a fixed or adjustable mechanical stop; or by applying an electrical impulse to the cantilevered probe array.

A cantilevered probe response is detected from at least one self-sensed cantilevered probe in the cantilevered probe array and the target chemical species is determined, as seen at block 128. Detecting the cantilevered probe response from one or more actuated cantilevered probes comprises, for example, measuring a shifted resonant frequency, a shifted Q factor, a shifted impedance, a shifted deflection amplitude, and a combination thereof. A fast Fourier transform (FFT) may be performed on the cantilevered probe response from one or more actuated cantilevered probes to detect the target chemical species. The target chemical species is determined based on the detected cantilevered probe response. The target chemical species may be determined based on comparing a measured shift from one or more actuated cantilevered probes to a reference set of cantilevered probe responses, and determining the target chemical species based on the reference set of cantilevered probe responses.

While the embodiments of the invention disclosed herein are presently considered to be preferred, various changes and modifications can be made without departing from the spirit and scope of the invention. The detailed description and drawings are merely illustrative of the invention rather than limiting, the scope of the invention being defined by the appended claims and equivalents thereof, and all variations and embodiments that come within the meaning and range of equivalents are embraced herein.

What is claimed is:

1. A chemical analysis system for detecting, identifying, and/or characterizing at least one target chemical species, comprising:
- a frequency-differentiated cantilevered probe array comprising a plurality of cantilevered probes, each cantilevered probe comprising:
  - a piezoelectric layer including a piezoelectric material that drives and senses the motion of the cantilevered probe;
  - a treated section, wherein the treated sections of the plurality of cantilevered probes are different from one another and include a chemical-sensitive coating material;
  - a first electrode electrically coupled to the piezoelectric layer; and
  - a second electrode electrically coupled to the piezoelectric layer;
- a first electrical lead electrically coupled to a first electrode of at least one of the plurality of cantilevered probes and in electrical communication with the first electrode of each of the plurality of cantilevered probes;
- a second electrical lead electrically coupled to a second electrode of at least one of the plurality of cantilevered probes and in electrical communication with the second electrode of each of the plurality of cantilevered probes;
- an interface circuit electrically coupled to the first and second electrical leads and configured to actuate the cantilevered probes;
- a sensing circuit electrically coupled to the first and second electrical leads; and
- wherein the cantilevered probes are actuated when, through the first and second leads, a drive voltage is applied to the piezoelectric layer by the interface circuit thus generating an electrical response transmitted to the sensing circuit and at least one cantilevered probe in the array exhibits a shifted electrical response when the cantilevered probe array is exposed to the target chemical species.

2. The chemical analysis system of claim 1 wherein the first and second electrodes of the plurality of cantilevered probes are electrically coupled to one another, the plurality of cantilevered probes thus being connected in series to the first and second leads.

3. The chemical analysis system of claim 1 wherein the cantilevered probe array comprises a network of series-connected and parallel-connected cantilevered probes electrically connected to a pair of cantilevered probe array drive pads.

4. The chemical analysis system of claim 1 wherein the interface circuit comprises an adjustable frequency generator that is scanned through a predetermined frequency range.

5. The chemical analysis system of claim 1 wherein the interface circuit comprises an impedance analyzer that is scanned through a resonant frequency of the at least one cantilevered probe in the cantilevered probe array.

6. The chemical analysis system of claim 1 wherein the interface circuit comprises an oscillator circuit operating at a resonant frequency of the at least one cantilevered probe in the cantilevered probe array.

7. The chemical analysis system of claim 1 wherein the interface circuit comprises an oscillator circuit operating at a predetermined frequency, wherein the predetermined frequency is off-resonance with respect to the at least one cantilevered probe in the cantilevered probe array.

8. The chemical analysis system of claim 1 wherein the interface circuit comprises an impulse circuit for applying an electrical impulse to the cantilevered probe array.

9. The chemical analysis system of claim 1 wherein the interface circuit includes a fast Fourier transform generator to perform a fast Fourier transform on the shifted cantilevered probe response.

10. The chemical analysis system of claim 1 wherein the interface circuit detects a shifted electrical response from the at least one actuated cantilevered probe.

11. The chemical analysis system of claim 10 wherein the shifted electrical response comprises one of a shifted resonant frequency, a shifted Q factor, a shifted impedance, and a shifted deflection amplitude.

12. The chemical analysis system of claim 1 further comprising: a controller in communication with the interface circuit; wherein the controller receives a shifted electrical response from a set of cantilevered probes in the cantilevered probe array, and wherein the target chemical species is determined based on the shifted electrical response.

13. The chemical analysis system of claim 1 further comprising: a controller in communication with the interface circuit; wherein the controller receives a shifted electrical response from a set of cantilevered probes in the cantilevered probe array, and wherein the target chemical species is determined based on a comparison between the shifted electrical response and a reference set of electrical responses.

14. The chemical analysis system of claim 13 wherein the reference set of electrical responses comprises measured responses from known exposure conditions.

15. The chemical analysis system of claim 1 wherein the chemical-sensitive coating material comprises a coating applied through a mask disposed on a portion of the at least one cantilevered probe.

16. The chemical analysis system of claim 1 wherein the chemical-sensitive coating material comprises a non-homogeneous coating material applied to a set of cantilevered probes in the cantilevered probe array.

17. The chemical analysis system of claim 1 further comprising: a reference cantilevered probe in the cantilevered probe array, wherein the reference cantilevered probe provides a reference electrical response when the cantilevered probe array is exposed to the target chemical species.

18. The chemical analysis system of claim 1 further comprising: a species attraction electrode disposed on the at least one cantilevered probe in the cantilevered probe array to allow application of a species attraction potential.

19. The chemical analysis system of claim 1, wherein a resistive heater is coupled to at least one cantilevered probe in the cantilevered probe array and the chemical detection system further comprises a heater circuit electrically coupled to the resistive heater.

20. A chemical analysis system for detecting, identifying, and/or characterizing at least one target chemical species, comprising:
- a frequency-differentiated cantilevered probe array comprising a plurality of cantilevered probes, each cantilevered probe comprising:
  - a piezoelectric layer including a piezoelectric material that drives and senses the motion of the cantilevered probe;
  - a treated section, wherein the treated sections of the plurality of cantilevered probes are different from one another and include a chemical-sensitive coating material;
  - a first electrode electrically coupled to the piezoelectric layer; and a second electrode electrically coupled to the piezoelectric layer;

a first electrical lead electrically coupled to a first electrode of each of the plurality of cantilevered probes and in electrical communication with the first electrode of each of the plurality of cantilevered probes;

a second electrical lead electrically coupled to a second electrode of each of the plurality of cantilevered probes and in electrical communication with the second electrode of each of the plurality of cantilevered probes, wherein the first and second leads thus are connected in parallel to the plurality of cantilevered probes;

an interface circuit electrically coupled to the first and second electrical leads and configured to actuate the cantilevered probes;

a sensing circuit electrically coupled to the first and second electrical leads; and wherein the cantilevered probes are actuated when, through the first and second leads, a drive voltage is applied to the piezoelectric layer by the interface circuit thus generating an electrical response transmitted to the sensing circuit and at least one cantilevered probe in the array exhibits a shifted electrical response when the cantilevered probe array is exposed to the target chemical species.

* * * * *